(12) United States Patent
Kurup et al.

(10) Patent No.: US 10,845,335 B2
(45) Date of Patent: Nov. 24, 2020

(54) ELECTROCHEMICAL TONGUE

(71) Applicant: University of Massachusetts, Boston, MA (US)

(72) Inventors: Pradeep Kurup, Nashua, NH (US); Ramaswamy Nagarajan, Westford, MA (US); Timothy Ponrathnam, Lowell, MA (US); Weeradech Kiratitanavit, Lowell, MA (US)

(73) Assignee: University of Massachusetts, Boston, MA (US)

( * ) Notice: Subject to any disclaimer, the term of this patent is extended or adjusted under 35 U.S.C. 154(b) by 234 days.

(21) Appl. No.: 15/923,698

(22) Filed: Mar. 16, 2018

(65) Prior Publication Data

US 2018/0246059 A1    Aug. 30, 2018

Related U.S. Application Data

(62) Division of application No. 14/782,215, filed as application No. PCT/US2014/032799 on Apr. 3, 2014, now abandoned.

(60) Provisional application No. 61/808,102, filed on Apr. 3, 2013.

(51) Int. Cl.
*G01N 27/48* (2006.01)
*G01N 33/18* (2006.01)

(52) U.S. Cl.
CPC ......... *G01N 27/48* (2013.01); *G01N 33/1813* (2013.01)

(58) Field of Classification Search
CPC ........ G01N 27/26; G01N 27/30; G01N 27/48; G01N 33/1813

USPC ....................... 205/789.5; 204/418
See application file for complete search history.

(56) References Cited

U.S. PATENT DOCUMENTS

| | | |
|---|---|---|
| 4,090,926 A | 5/1978 | Matson |
| 4,146,436 A | 3/1979 | Kellermann et al. |
| 4,374,041 A | 2/1983 | Matson |
| 4,426,621 A | 1/1984 | Galwey et al. |
| 4,543,216 A | 9/1985 | Ishikura et al. |
| 5,292,423 A | 3/1994 | Wang |
| 5,310,687 A | 5/1994 | Bard et al. |
| 5,497,091 A | 3/1996 | Bratton et al. |
| 5,519,147 A | 5/1996 | Swager et al. |
| 5,676,820 A * | 10/1997 | Wang .................... G01N 27/42 204/403.14 |

(Continued)

FOREIGN PATENT DOCUMENTS

| | | |
|---|---|---|
| WO | 99/13325 A1 | 3/1999 |
| WO | 2014/165659 A2 | 10/2014 |

OTHER PUBLICATIONS

Stern et al., "Electropolynnerization on Microelectrodes: Functionalization Technique for Selective Protein and DNA Conjugation", Analytical Chemistry, vol. 78, No. 18, 2006, All Pages. (Year: 2006).*

(Continued)

*Primary Examiner* — Daniel P Malley, Jr.
(74) *Attorney, Agent, or Firm* — Hamilton, Brook, Smith & Reynolds, P.C.

(57) ABSTRACT

An electrochemical tongue can be used for detection of metal ions. The reference electrode of the electrochemical tongue can be coated with a polymer. More than one reference electrode can be used, and the electrochemical tongue can be inserted into a cone penetrometer for portable, in situ analysis.

18 Claims, 25 Drawing Sheets

(56) References Cited

U.S. PATENT DOCUMENTS

| | | | |
|---|---|---|---|
| 5,798,940 | A | 8/1998 | Bratton et al. |
| 5,865,972 | A | 2/1999 | Buffle et al. |
| 6,018,389 | A | 1/2000 | Kyle et al. |
| 6,097,785 | A | 8/2000 | Elam |
| 6,115,061 | A | 9/2000 | Lieberman et al. |
| 6,436,259 | B1 | 8/2002 | Russell |
| 6,682,647 | B1 | 1/2004 | Wang |
| 6,730,201 | B1 | 5/2004 | Kuhlman et al. |
| 6,875,337 | B1 | 5/2005 | Schroder et al. |
| 7,452,452 | B2 | 11/2008 | Ren et al. |
| 7,534,560 | B2 | 5/2009 | Lu et al. |
| 7,625,469 | B1 | 12/2009 | Yelton et al. |
| 8,098,148 | B2 | 1/2012 | Park et al. |
| 8,114,955 | B2 | 2/2012 | Ying et al. |
| 8,152,977 | B2 | 4/2012 | Bourgerette et al. |
| 2004/0042931 | A1 | 3/2004 | Wit et al. |
| 2005/0008860 | A1* | 1/2005 | Garnier ............... C08G 61/124 428/403 |
| 2006/0185977 | A1 | 8/2006 | Wide et al. |
| 2007/0278096 | A1* | 12/2007 | Viltchinskaia ..... G01N 33/1813 204/400 |
| 2011/0186449 | A1 | 8/2011 | Clochard et al. |
| 2011/0284395 | A1* | 11/2011 | Dimitrakopoulos ... G01N 27/42 205/789 |
| 2011/0308942 | A1 | 12/2011 | Liu et al. |
| 2013/0248378 | A1* | 9/2013 | Kanemoto ............. G01N 27/30 205/641 |

OTHER PUBLICATIONS

Ponrathnam et al., "Detection of Cadmium using Conjugated Polymer Modified Electrodes", 2012, Materials Research Society, vol. 1436, All Pages. (Year: 2012).*

Browning, "Electrometric Methods", 1969, pp. 82-89. (Year: 1969).*

STN Structure search 15923698, 2020, STIC, All Pages. (Year: 2020).*

International Search Report and the Written Opinion of the International Searching Authority, or the Declaration, Application No. PCT/US2014/032799, "An Electrochemical Tongue," International Filing Date: Apr. 3, 2014, dated Nov. 24, 2014.

Kounaves, "Handbook of Instrumental Techniques for Analytical Chemistry," Prentice Hall PTR, 709-725.

Kurup and Nagarajan, "A Hybrid Electronic Tongue for Geoenvironmental Site Characterization," presented at CMMI Conference, 2012.

Kurup, "Novel Technologies for sniffing soil and ground water contaminants," Current Science, vol. 97, No. 8, 2009.

Li et al., "Nanostructured Sensors for Detection of Heavy Metals: A Review," ACS Sustainable Chem. Eng., 1: 713-723, 2013.

Ponrathnam et al., "Detection of Cadmium using Conjugated Polymer Modified Electrodes," Mater. Res. Soc. Symp. Proc., vol. 1436, Materials Research Society, 2012.

Prakash et al., "Copper(II) ion sensor based on electropolymerized undoped conducting polymers," J. Solid State Electrochem, 6:203-208, 2002.

Stern et al., "Electropolymerization on Microelectrodes: Functionalization Technique for Selective Protein and DNA Conjugation," Anal. Chem, 78(18): 6340-6346, 2006.

US EPA, "National Primary Drinking Water Regulations," Washington GPO: May 2009.

PCT/US2014/032799 Notification Concerning Transmittal of International Report on Patentability dated Oct. 15, 2015 entitled "An Electrochemical Tongue".

Long et al., "Amperometric hydrogen peroxide sensor electrodes coated with electropolymerized tyrosine derivative and phenolic films", 2001, Journal of Electroanalytical Chemistry 501, 107-113, 2001.

Metrohm, "Determination of Zinc, Cadmium, Lead and Copper in Effluent Sample," VA Application Work AW UK4-0185, 2007.

Pine Instrument Company, "Educator's Reference Guide for Electrochemistry," 42-45, 2000.

An et al., "Enhanced sensitivity of a gas sensor incorporating single-walled carbon nanotube-polypyrrole nanocomposites," Advanced Materials 16:12, 1005-1009, 2004.

Maksymiuk, K., "Chemical Reactivity of Polypyrrole and Its Relevance to Polypyrrole Based Electrochemical Sensors," Electroanalysis 18:16, pp. 1537-1551, 2006.

Pihel et al., "Overoxidized Polypyrrolye-Coated Carbon Fiber Microelectrodes for Dopamine Measurements with Fast-Scan Cyclic Voltammetry," Analytical Chemistry, 68:13, 2084-2089, 1996.

Rahman et al., "Characterization of an EDTA Bonded Conducting Polymer Modified Electrode: Its Application for the Simultaneous Determination of Heavy Metal Ions," Analytical Chemistry, 75:5, 1123-1129, 2003.

Tamer et al., "A Selective Film Based on Poly (3-octylthiophene) Doped with Dihydroxyanthraquinone Sulfonate," Electroanalysis 20, No. 16, 1805-1810, 2008.

Tang et al., "Strategy for Sensor Based on Fluorescence Emission Red Shift of Conjugated Polymers: Applications in pH Response and Enzyme Activity Detection," Anal. Chem., 85, 825-830, 2013.

Wang et al., "Carbon Nanotube/Polythiophene Chemiresistive Sensors for Chemical Warfare Agents," J. Am. Chem. Soc., 130, 5392-5393, 2008.

Zanganeh, A. and Amini, M., "Polypyrrole-modified electrodes with induced recognition sites for potentiometric and voltammetric detection of copper(II) ion," Sensors and Actuators B 135, 358-365, 2008.

Zanganeh, A. and Amini, M., "A potentiometric and voltammetric sensor based on polypyrrole film with electrochemically induced recognition sites for detection of silver ion," Electrochimica Acta 52, 3822-3830, 2007.

Zejli et al., "Stripping voltammetry of silver ions at polythiophene-modified platinum electrodes," Talanta 71,1594-1598, 2007.

* cited by examiner

Section A-A

FIG. 6A

ELECTROCHEMICAL TONGUE

RELATED APPLICATIONS

This application is a divisional of U.S. application Ser. No. 14/782,215, which is the U.S. National Stage of International Application No. PCT/US2014/032799, filed on Apr. 3, 2014, which designates the U.S., published in English, and claims the benefit of U.S. Provisional Application No. 61/808,102, filed on Apr. 3, 2013. The entire teachings of the above applications are incorporated herein by reference.

GOVERNMENT SUPPORT

This invention was made with Government support under NSF-CMMI-1031505 from the National Science Foundation. The Government has certain rights in the invention.

BACKGROUND OF THE INVENTION

Known methods used for the detection of trace concentrations of metal ion contaminants generally utilize sophisticated analytical tools such as atomic absorption spectroscopy (AAS) and inductively coupled plasma mass spectrometry (ICPMS). These techniques, while extremely sensitive, require expensive instrumentation and highly trained personnel. In addition, they are frequently non-portable, which severely limits their suitability for on-site detection of metal ions. Test solutions must be sampled at the contamination site and then shipped off-site to a lab, where they are tested using the techniques mentioned above. For these reasons, the tests are expensive and can potentially expose laboratory personnel to hazardous materials.

Highly sensitive chemical sensing systems integrated within direct push technologies (DPTs), such as a cone penetrometer (CPT) or membrane interface probe (MIP), have become valuable tools for contaminant characterization in complex soil matrices. By providing the possibility for rapid, real-time, on-site analysis, a CPT instrumented with sensors can serve to ensure the safety of laboratory personnel and field workers by minimizing exposure to contaminated soil samples. In recent years, a deviation from these techniques has been presented through a multitude of sensors and sensing systems integrated within DPTs, but issues of simplistic system design, cost, functionality and efficiency have yet to be overcome. Existing systems are often relatively complex, do not accommodate both qualitative and quantitative analysis of inorganic species, and require highly trained operators. In particular, these systems may not detect metal ions at a sufficiently low concentration. In other words, the sensitivity is insufficient.

Thus, there is a need in the art for a system that can detect metal ions at a lower level of detection. Preferably, such a system would be portable, in order to provide qualitative and quantitative in situ determination of the metal contaminants in groundwater and saturated soil.

SUMMARY OF THE INVENTION

Disclosed herein is an electrochemical tongue. The electrochemical tongue can include a reference electrode, a counter electrode, one or more working electrodes, wherein at least one of the one or more working electrodes is coated with a polymer or copolymer having the formula (I):

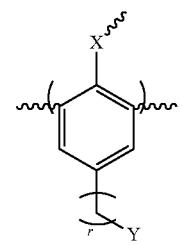

X can be independently NH or O; r can be independently an integer from approximately 1 to approximately 15; and Y can be chelating agent. The electrochemical tongue can also include a potentiostat in electrical communication with the reference electrode, the counter electrode, and the one or more working electrodes. The electrochemical tongue can also have at least two working electrodes that are of distinct materials. One or more working electrodes can be formed from gold, carbon fiber, silver, platinum, and transparent conductive oxides. At least one of the one or more working electrodes can be of glassy carbon, carbon paste, carbon fiber, carbon nanotubes, and graphene. One of the one or more working electrodes can include conductive metal oxides coated on rigid or flexible substrates. At least one of the working electrodes can be coated with a polymer having the formula (II):

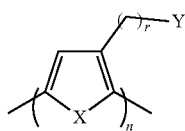

X can be NH or O; r can be an integer from approximately 1 to approximately 15; n can be an integer from approximately 6 to approximately 100; and Y can be a chelating agent. At least one of the at least two working electrodes is coated with a polymer having the formula (III):

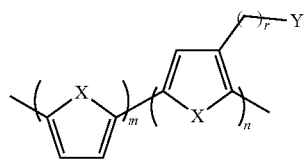

X can be NH or O; r can be a number of methylene groups between 1 and 15; m can be an integer from approximately 6 to approximately 100; n can be an integer from approximately 6 to approximately 100; and Y can be a chelating agent. Preferably, the sum of m+n is at least 10. The chelating agent Y can be an aminocarboxylic acid; a hydrocarboxylic acid; ethelene diamine; diethylenetriamine; triethylenetetramine; triaminotriethylamine; polyethyleneimine; triethanolamine; n-hydroxyethylethylene diamine; 2-aminopyridine; 4-aminopyridine; 2,2' dipicolylamine; 5,6 diamino-1,10 phenanthroline; thioglycolic acid; gluthathione; or diethyl dithiophosphoric acid. In particular, the chelating agent Y is an aminocarboxylic acid. The aminocarboxylic acid is an iminodiacetic acid or n-hydroxyethyl glycine. The chelating agent Y is a hydroxycarboxylic acid. The hydroxycarboxylic acid can be tartaric acid, citric acid, or gluconic acid. The electrochemical tongue can further include one or more of a voltammetric sensor, an amperometric sensor, and a potentiometric sensor. The voltammetric sensor includes one or more of a linear sweep sensor, a cyclic sensor, a stair case sensor, a differential pulse sensor, a square wave sensor, and an anodic/cathodic stripping voltammetry sensor. The electrochemical tongue can further include a potentiometric sensor. The electrochemical tongue can further include one or more of an redox sensor, a pH sensor, an electrical conductivity/sensitivity sensor, a dissolved oxygen sensor, and a selective ion selective sensor. The electrochemical tongue can further include a housing defining a passageway for the reference electrode, counter electrode, and one or more working electrodes. The housing can be adapted for insertion into a penetrometer. The electrochemical tongue can further include a porous portion that allows a sample to enter the electrochemical tongue. At least a portion of at least one of the one or more working electrodes can include sensing surfaces that have been modified by at least one of gel integration and bismuth/mercury coating. The one or more of the working electrodes can have an ionically conductive fluoropolymer overcoating. The electrochemical tongue can further include a processor programmed to receive a voltammetric response, filter and extract features, build a decision tree and a linear model, and display the identity of a metal ion.

Disclosed herein is also a method for performing voltammetry. The method includes contacting a sample to be analyzed with an electrochemical tongue, applying a constant voltage across the one or more of the working electrodes to reduce the metal ion onto the surface of the electrode, and increasing the voltage across one or more working electrode to oxidize and strip off the metal from the surface of the electrode. The electrical tongue can include a reference electrode, a counter electrode, one or more working electrodes, and a potentiostat in electrical communication with the reference electrode, the counter electrode, and the one or more working electrodes. At least one of the one or more working electrodes can be coated with a polymer or copolymer having the following formula (I):

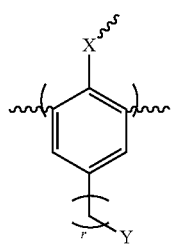

The variable X can be independently NH or O; r can be independently an integer from approximately 1 to approximately 15; and Y can be a chelating agent. The electrochemical tongue can have at least two working electrodes of distinct materials to which the sample is contacted. At least one of the one or more working electrodes can be from gold, carbon fiber, silver, platinum, and transparent conductive oxides. At least one of the one or more working electrodes to which a sample is contacted can be of glassy carbon, carbon paste, carbon fiber, carbon nanotubes, or graphene. At least one of the working electrodes to which a sample is contacted can include conductive metal oxides coated on rigid or flexible substrates. At least one of the at least two working electrodes to which a sample is contacted is coated with a polymer having the formula (II):

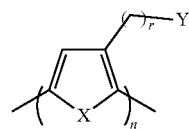

The variable X can be NH or O; r can be an integer from approximately 1 to approximately 15; n can be an integer from approximately 6 to approximately 100; and Y can be a chelating agent. At least one of the at least two working electrodes to which a sample is contacted can be coated with a polymer having the formula (III):

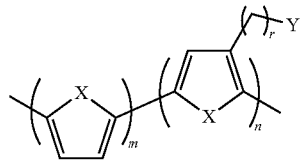

The variable X can be NH or O; r can be an integer from approximately 1 to approximately 15; m can be an integer from approximately 6 to approximately 100; n can be an integer from approximately 6 to approximately 100; and Y can be a chelating agent. Preferably, the sum of m+n is at least 10. The chelating agent Y coating the one or more working electrodes to which a sample is in contact can be an aminocarboxylic acid; a hydrocarboxylic acid; ethelene diamine; diethylenetriamine; triethylenetetramine; triaminotriethylamine; polyethyleneimine; triethanolamine; n-hydroxyethylethylene diamine; 2-aminopyridine; 4-aminopyridine; 2,2' dipicolylamine; 5,6 diamino-1,10 phenanthroline; thioglycolic acid; gluthathione; or diethyl dithiophosphoric acid. In particular, the chelating agent Y can be an aminocarboxylic acid. The aminocarboxylic acid can be an iminodiacetic acid or n-hydroxyethyl glycine. The chelating agent Y can be a hydroxycarboxylic acid. The hydroxycarboxylic acid can be tartaric acid, citric acid, or gluconic acid. The method can further include measuring a first sampling current that flows through the one or more working electrodes during a predetermined interval in which the pulse voltage is not applied, measuring a second sampling current that flows through the one or more working electrodes while the pulse voltage is applied, and calculating the difference between the first and second sampling currents.

Disclosed herein is also a method for performing voltammetry. The method includes contacting a sample to be analyzed with an electrochemical tongue, and ramping the working electrode voltage linearly versus time to either positive or negative voltages. The electrical tongue can include a reference electrode, a counter electrode, one or more working electrodes, and a potentiostat in electrical communication with the reference electrode, the counter electrode, and the one or more working electrodes. At least one of the one or more working electrodes can be coated with a polymer or copolymer having the following formula (I):

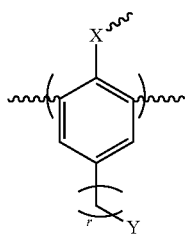

The variable X can be independently NH or O; r can be independently an integer from approximately 1 to approximately 15; and Y can be a chelating agent. The electrochemical tongue can have at least two working electrodes of distinct materials to which the sample is contacted. At least one of the one or more working electrodes can be from gold, carbon fiber, silver, platinum, and transparent conductive oxides. At least one of the one or more working electrodes to which a sample is contacted can be of glassy carbon, carbon paste, carbon fiber, carbon nanotubes, or graphene. At least one of the working electrodes to which a sample is contacted can include conductive metal oxides coated on rigid or flexible substrates. At least one of the at least two working electrodes to which a sample is contacted is coated with a polymer having the formula (II):

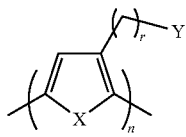

The variable X can be NH or O; r can be an integer from approximately 1 to approximately 15; n can be an integer from approximately 6 to approximately 100; and Y can be a chelating agent. At least one of the at least two working electrodes to which a sample is contacted can be coated with a polymer having the formula (III):

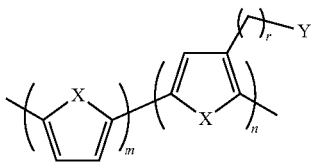

The variable X can be NH or O; r can be an integer from approximately 1 to approximately 15; m can be an integer from approximately 6 to approximately 100; n can be an integer from approximately 6 to approximately 100; and Y can be a chelating agent. Preferably, the sum of m+n is at least 10. The chelating agent Y coating the one or more working electrodes to which a sample is in contact can be an aminocarboxylic acid; a hydrocarboxylic acid; ethelene diamine; diethylenetriamine; triethylenetetramine; triaminotriethylamine; polyethyleneimine; triethanolamine; n-hydroxyethylethylene diamine; 2-aminopyridine; 4-aminopyridine; 2,2' dipicolylamine; 5,6 diamino-1,10 phenanthroline; thioglycolic acid; gluthathione; or diethyl dithiophosphoric acid. In particular, the chelating agent Y can be an aminocarboxylic acid. The aminocarboxylic acid can be an iminodiacetic acid or n-hydroxyethyl glycine. The chelating agent Y can be a hydroxycarboxylic acid. The hydroxycarboxylic acid can be tartaric acid, citric acid, or gluconic acid. The method can further include measuring a first sampling current that flows through the one or more working electrodes during a predetermined interval in which the pulse voltage is not applied, measuring a second sampling current that flows through the one or more working electrodes while the pulse voltage is applied, and calculating the difference between the first and second sampling currents.

As described herein, the portable electrochemical tongue provides numerous benefits. Providing a polymer coating on the working electrode improves the sensitivity and lowers the level of detection. Providing an electrochemical tongue having more than one working electrode further improves the ability to detect metal ions in complex mixtures, such as in groundwater analysis. Further, an electrochemical tongue provides improved sensitivity in a device that is more portable than traditional analytical systems, such as atomic absorption spectroscopy and inductively coupled plasma mass spectrometry. Such in situ analysis can offer significant cost savings because it permits on site detection in a single step. Paired with a processor adapted for machine learning, such a device can improve the speed and accuracy of on-site detection.

BRIEF DESCRIPTION OF THE DRAWINGS

Figure 6A:
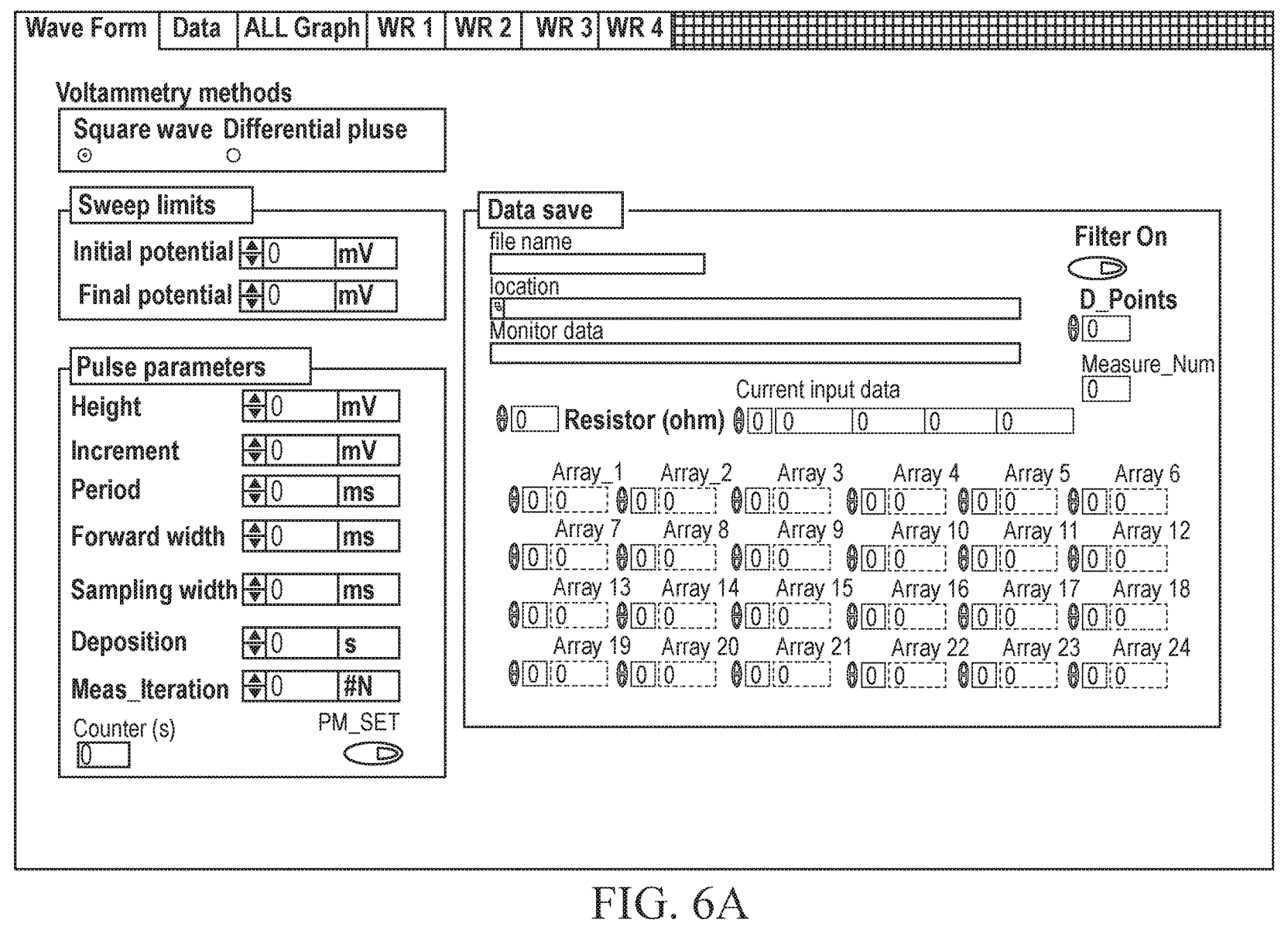

FIGS. 6A-6D are images of a virtual instrument (VI) for data extraction and management suitable for use with an electronic tongue.

DETAILED DESCRIPTION OF THE INVENTION

Figures 1A, 1B, 1C:
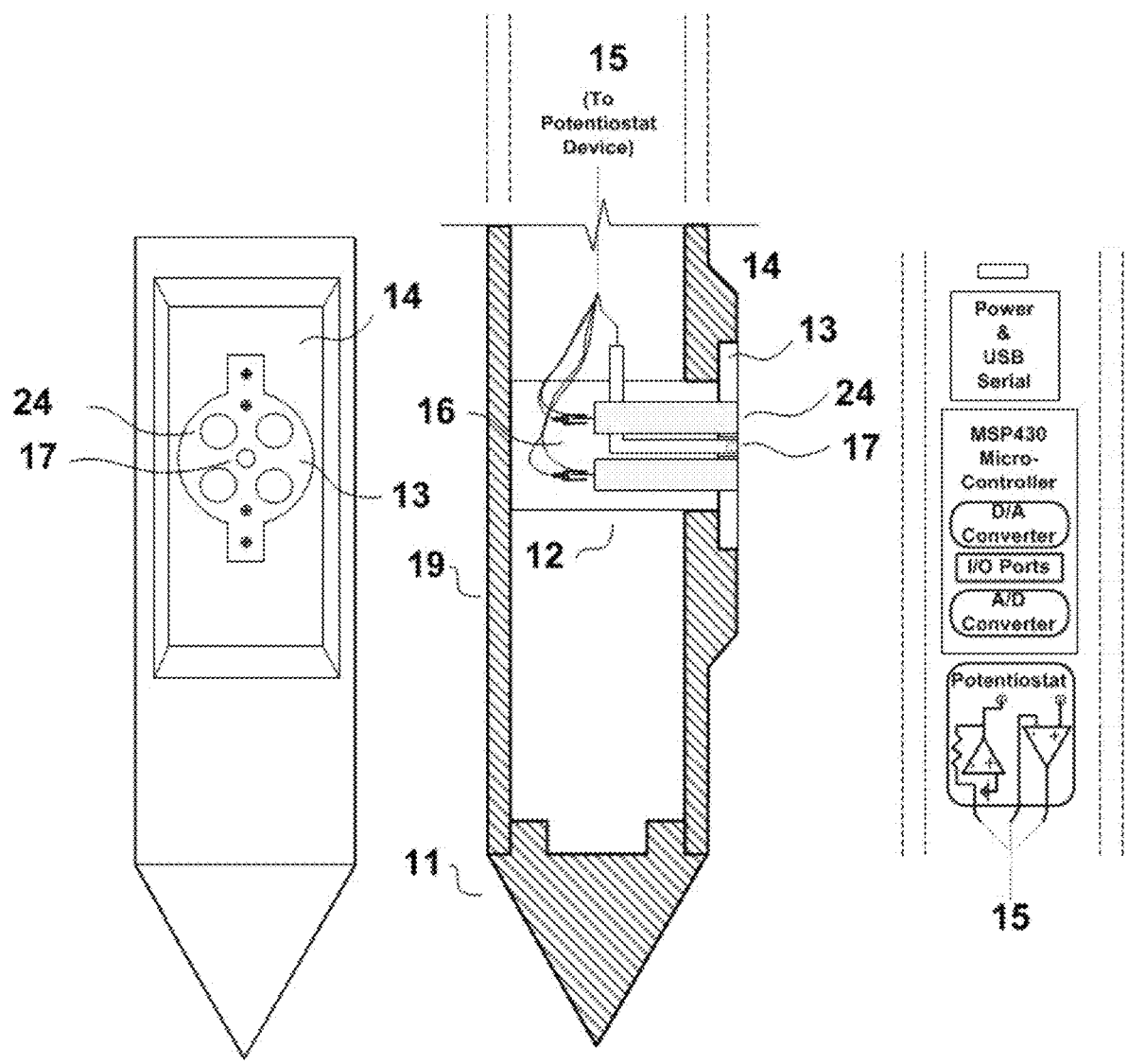
FIG. 1A is a front view of one embodiment of a non-sampling electronic tongue penetrometer.
FIG. 1B is a side cross section of the non-sampling electronic tongue penetrometer of FIG. 1A.
FIG. 1C is a detail of a general schematic of down-hole potentiostat device component of the electrochemical tongue of FIGS. 1A and 1B.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

Described herein is an exemplary electrochemical tongue having a reference electrode, a counter electrode, and one or more working electrodes. A potentiostat can be in electrical communication with the reference electrode, counter electrode, and one or more working electrodes. The working electrode can be coated with a polymer having the formula (I):

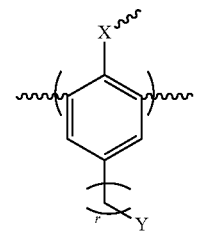

The variable X can be NH or O. The variable r can be an integer from approximately 1 to approximately 15. The variable Y is a chelating agent.

In one embodiment, X is oxygen, r is 1, and Y is a carboxylic acid, which yields a compound having the following structural formula (IV):

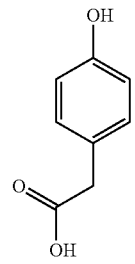 [SMILES: O=C(O)Cc1ccc(O)cc1]

The phenol can be polymerized from phenol monomers using chemical catalysts, enzyme catalysts (such as Horseradish peroxidase (HRP)), or biomimetic catalysts (such as Iron Salen). In biomimetic and enzyme catalyzed synthesis, the polymerization is initiated by the addition of hydrogen peroxide, which also acts as an oxidant. The monomer can also be polymerized by electrochemical polymerization using cyclic voltammetry. For example, the polymer can be electrochemically polymerized, yielding the following polymer coating on the electrode, where n can be an integer from approximately 6 to approximately 100:

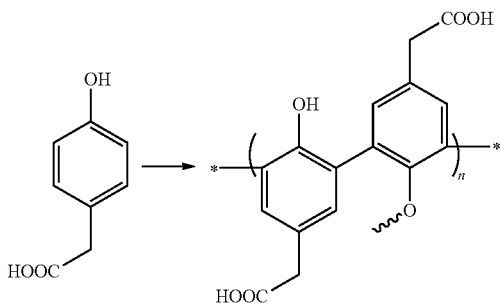

The electrodes can be formed of diverse materials and have many suitable geometries. The electrodes can be of gold, carbon fiber, silver, platinum, or transparent conductive oxides, or any other suitable material. The electrodes can be microelectrodes.

In a specific embodiment, the electrochemical tongue of the invention described herein can be inserted into a cone penetrometer, as an embodiment of the invention that is referred to as an "electronic tongue" or simply an "E-tongue." Inserting the electrochemical tongue into a cone penetrometer can provide a device for rapid, real-time analysis of electro-active species in complex subsurface strata.

An exemplary E-tongue of the invention has an electrochemical tongue as described herein integrated within a standard cone penetrometer. The E-tongue can include non-sampling and/or sampling sensors. In a non-sampling E-tongue, the working and reference electrodes directly can directly contact the sample (e.g., soil having water with heavy metal contaminants). The non-sampling sensors are located on the conical tip or along the sleeve of the probe, exposed to the soil, where voltammetric analysis is performed for identification and quantification of toxic metals at the electrode/soil interface. The electrodes for the non-sampling tongue should be robust because they directly contact the soil as the probe is pushed through the soil, and the friction can abrade the sensing surface of the electrode. The sampling sensors involve a system that draws contaminated water into the cone body (and brought in contact with the electrode array) under hydrostatic head or vacuum pressure across a porous filter.

Increased sensitivity, particularly for the detection of a plurality of analytes, can be improved by providing two or more working electrodes. While not all working electrodes need a conductive polymer coating, providing additional working electrodes with such a polymer coating can further improve sensitivity.

An exemplary E-tongue of the invention is illustrated in FIGS. 1A-1C. The cone penetrometer has a conical tip 11 and cylindrical tube 19. An exemplary cone penetrometer is described is ASTM D3441-05. The cone penetrometer is typically 3.57 cm in diameter with a 60 degree conical tip.

The cone penetrometer is designed to house various electrode arrangements and geometries. The welded steel section 14 extends the outer diameter to fit a multitude of sensing systems, additionally creating a flat surface for mounting electrodes 24 and 17. Section 14 is not necessary where sensors do not require a flat surface or additional area within the penetrometer. Section 14 includes a cylindrical extrusion to allow the sensor housing 12 to mount in position. The sensor housing can be fabricated from steel with insulation positioned at connector pins 21 and lead wires 16, eliminating possible short circuiting, or made of non-conducting materials such as high-density polyethylene. The exterior mounting bracket 13 serves to fixate the electrode housing 12 along the welded steel section 14. Preferably, the mounting bracket 13 is approximately ⅛th inch thick and consists of steel or high strength non-conducting materials (e.g. polycarbonate). The cylindrical extrusions 25 can serve as openings for working electrodes 24 and a reference electrode 17. Alternatively, cylindrical extrusion 25 can include a porous membrane and/or salt bridge to protect electrodes 17 and 24 (with electrodes recessed into the probe). As described herein, electrodes 24 can be coated with a polymer.

Optionally, a vibration dampening system 22 can be included to compensate for external vibrations. The vibration dampening system 22 can be a rubber mount or spring system that reduces resonant vibrations transmitted throughout the cone shaft to the electrochemical sensor array.

Figure 2A:
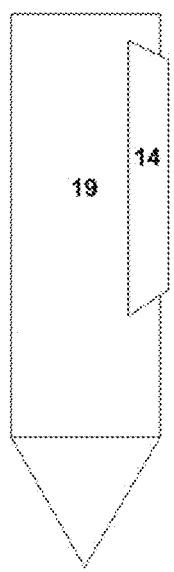
FIG. 2A is a side view of another embodiment of a non-sampling electronic tongue penetrometer.
Figure 2B:
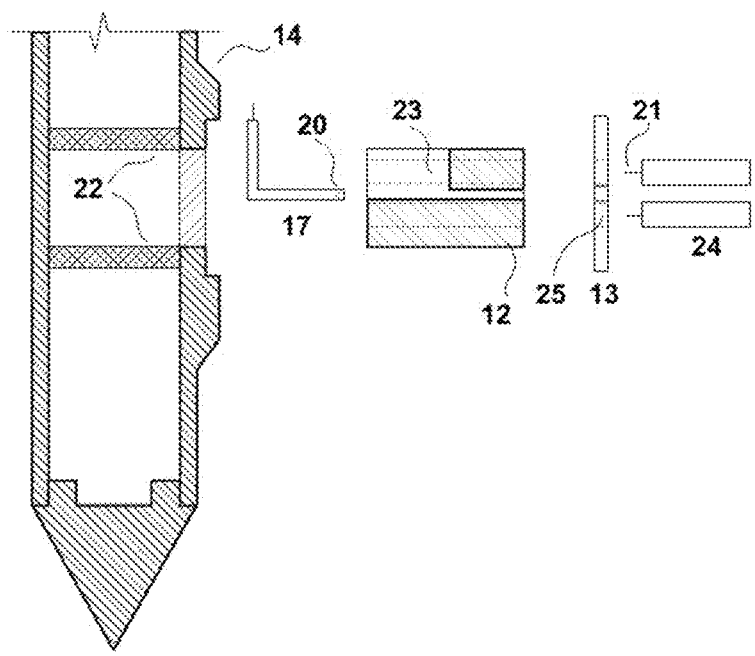
FIG. 2B is a side cross-section of the non-sampling electronic tongue penetrometer of FIG. 2A displaying detailed components extracted (from left to right: optional vibration dampening system, reference electrode, electrode housing, exterior mounting bracket, and working electrodes).

The reference electrode 17 is designed for stability, and should not contain toxic materials (such as a saturated calomel electrode) to prevent possible in situ contamination. As shown in FIGS. 2A-2B, the reference is a Ag/AgCl electrode, with a leakless frit 20 exposed to the soil. This electrode includes a 90 degree bend in the body to uphold stability while remaining compact in the space provided in the penetrometer. The electrode housing 12 should provide a space 23 for the reference electrode to slide in and out with ease for the non-sampling probe. A straight reference electrode can be used for the sampling probe, as long as the conductive frit 20 is exposed to the sampled water. The counter electrode can be any exposed conductive material, such as the penetrometer sleeve 19 for the non-sampling probe or the double threaded stud 26 for the sampling probe.

Figure 3A:
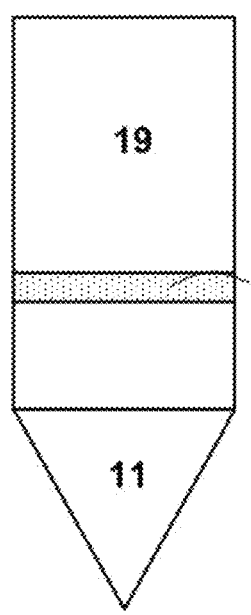
FIG. 3A is a front view of an embodiment of a sampling electronic tongue penetrometer.
Figure 3B:
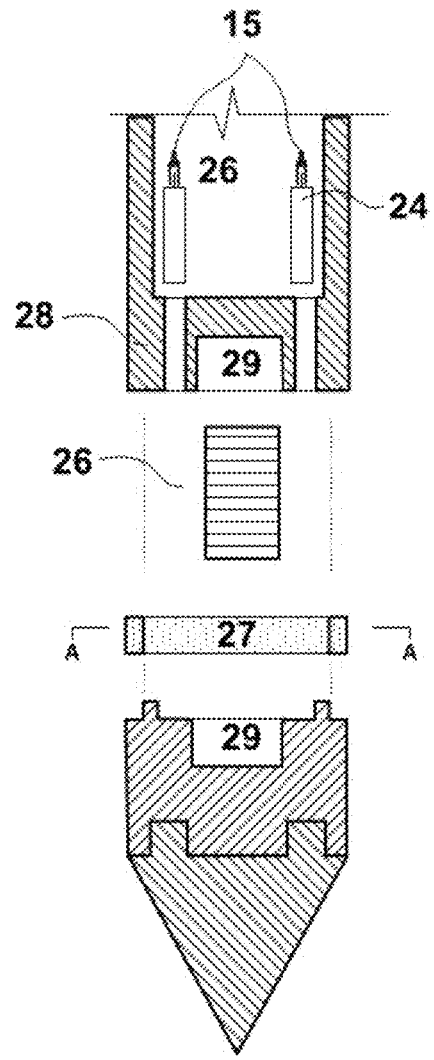
FIG. 3B is a cross-section of the sampling electronic tongue penetrometer as represented in FIG. 3A.
Figure 3C:
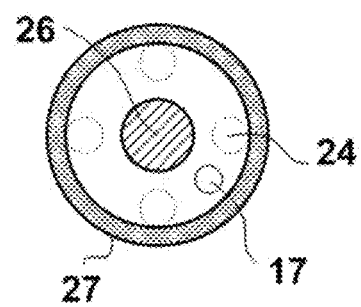
FIG. 3C is a plan view in cross-section, of the electronic tongue penetrometer as represented in FIGS. 2A and 2B.

An exemplary sampling probe is illustrated in FIGS. 3A-3C. In a sampling probe, the heavy metal contaminated fluid (e.g., from within the soil) is sampled through a porous filter into the interior of the device where the electrodes are located. In this configuration, the electrodes are less prone to damage because they are more protected. A porous ring 27 allows an analyte, such as contaminated water, to flow into an electrochemical tongue located within the probe body. The porous ring 27 can be constructed of a porous metal alloy, stone, or plastic. In a preferred embodiment, the thickness of the porous ring is approximately ⅛th inch. Contaminated water can flow across the porous boundary under hydrostatic pressure or suction (e.g., generated from vacuum, peristaltic, or diaphragm pumping systems) within the cone body. A double threaded stud 26 can hold the penetrometer body together while holding the porous ring in place at the female threaded sections 29. The threaded stud 26 can be hollow to allow electrical wires to pass through. Additionally, the threaded stud 26 can be used as a counter electrode within the electrochemical tongue. One of skill in the art will recognize, however, that the counter electrode need not be threaded. One or more working electrodes 24 and a reference electrode 17 can be housed in any location within the electrochemical tongue, exposed to the sampled groundwater, as shown in cross-section A-A of FIGS. 3A-3C. The sensor housing 28 serves to hold electrodes in place, while insulating connector pins 21 and lead wires 16.

The sensing materials used for working electrodes 24 generally are essentially electrochemically inert over a wide range of potentials. These materials are not intended to optimize resulting current signals nor achieve selectivity toward any one ion. Rather, the aim is to incorporate a sensor array of two or more electrodes with the choice of electrodes based on ruggedness (durability for field use), stability, and high cross-sensitivity.

Preferably, each sensor in the array produces a different response to the same set of analytes. The combined response from the sensor array should produce a stable integrated response representing the signature for the particular analyte that is sensed. These electrodes can be fabricated in any way to provide a robust sensing surface (e.g. mechanically, micro-nano pipetting, ink jetting, or lithographically).

The potentiostat device 15 can be designed to fit within the cone body, adjacent to the electrodes. This configuration is referred to as down-hole control. Alternatively, the potentiostat can be positioned at a location independent of, and far away from, the multi-sensor array, such as at the ground surface or next to a computer). The potentiostat system should preferably accommodate voltage waveforms and current ranges required for the incorporated electrode array. Exemplary constructions are provided in U.S. Pat. Nos. 8,152,977 and 4,426,621, the teachings of which are incorporated by reference in their entirety.

Figure 4:
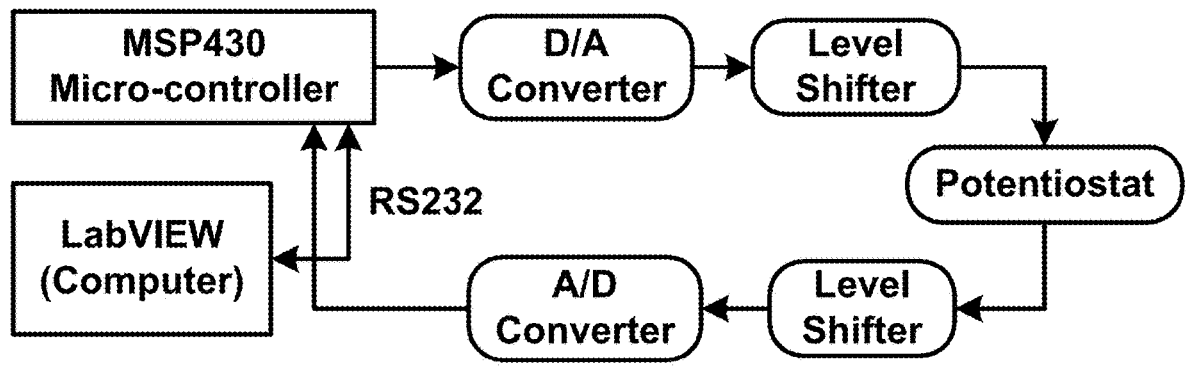
FIG. 4 is block diagram for a microcontroller controlled potentiostat system suitable for use with an electronic tongue as disclosed herein.
Figure 5:
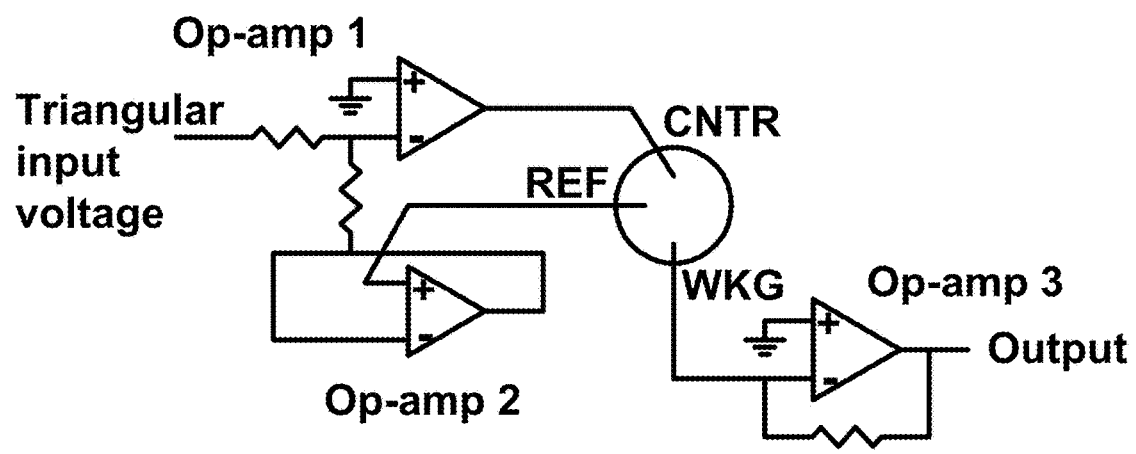
FIG. 5 is a schematic for a potentiostat circuit suitable for use with an electronic tongue.
Figure 6B:
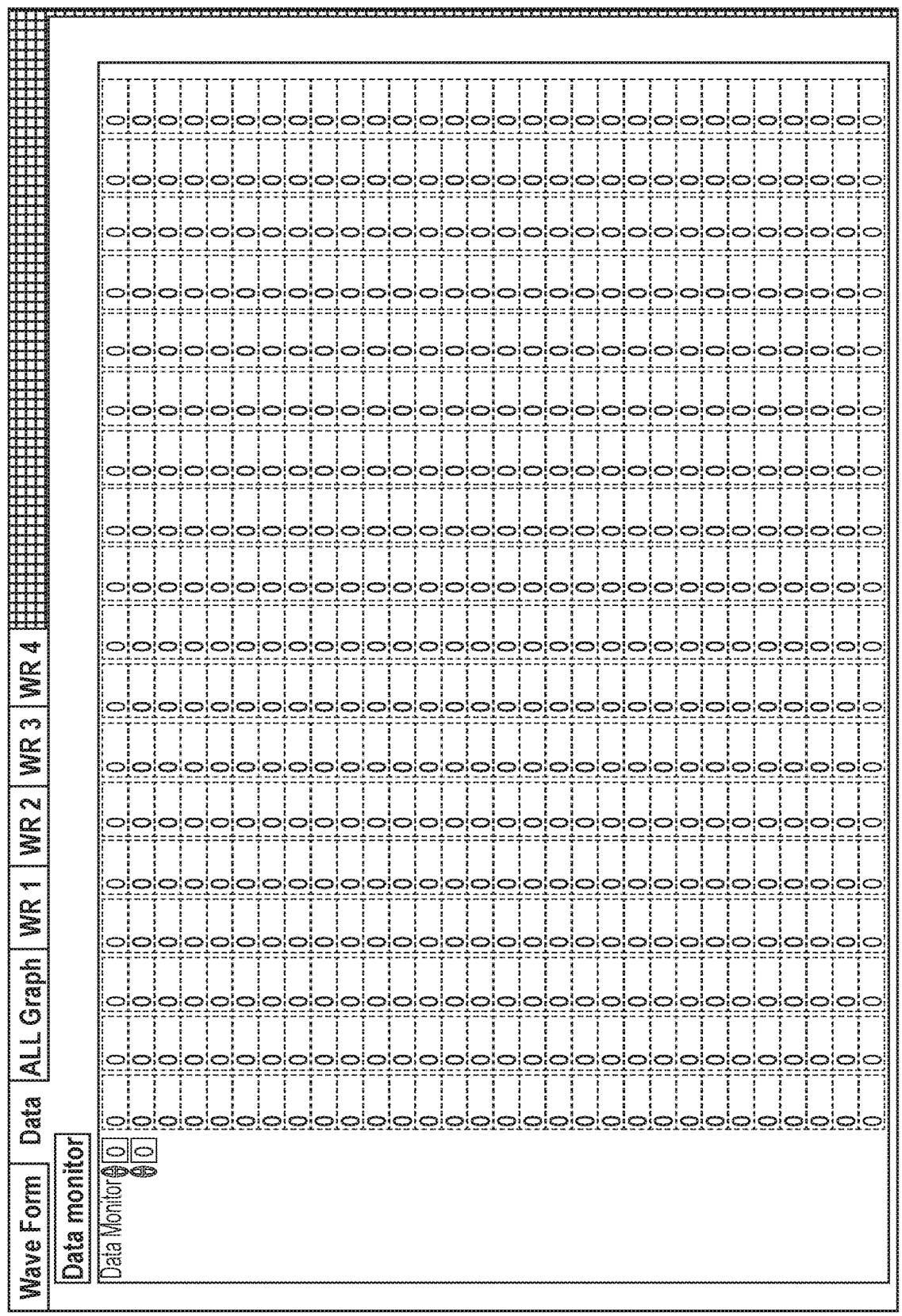
Figure 6C:
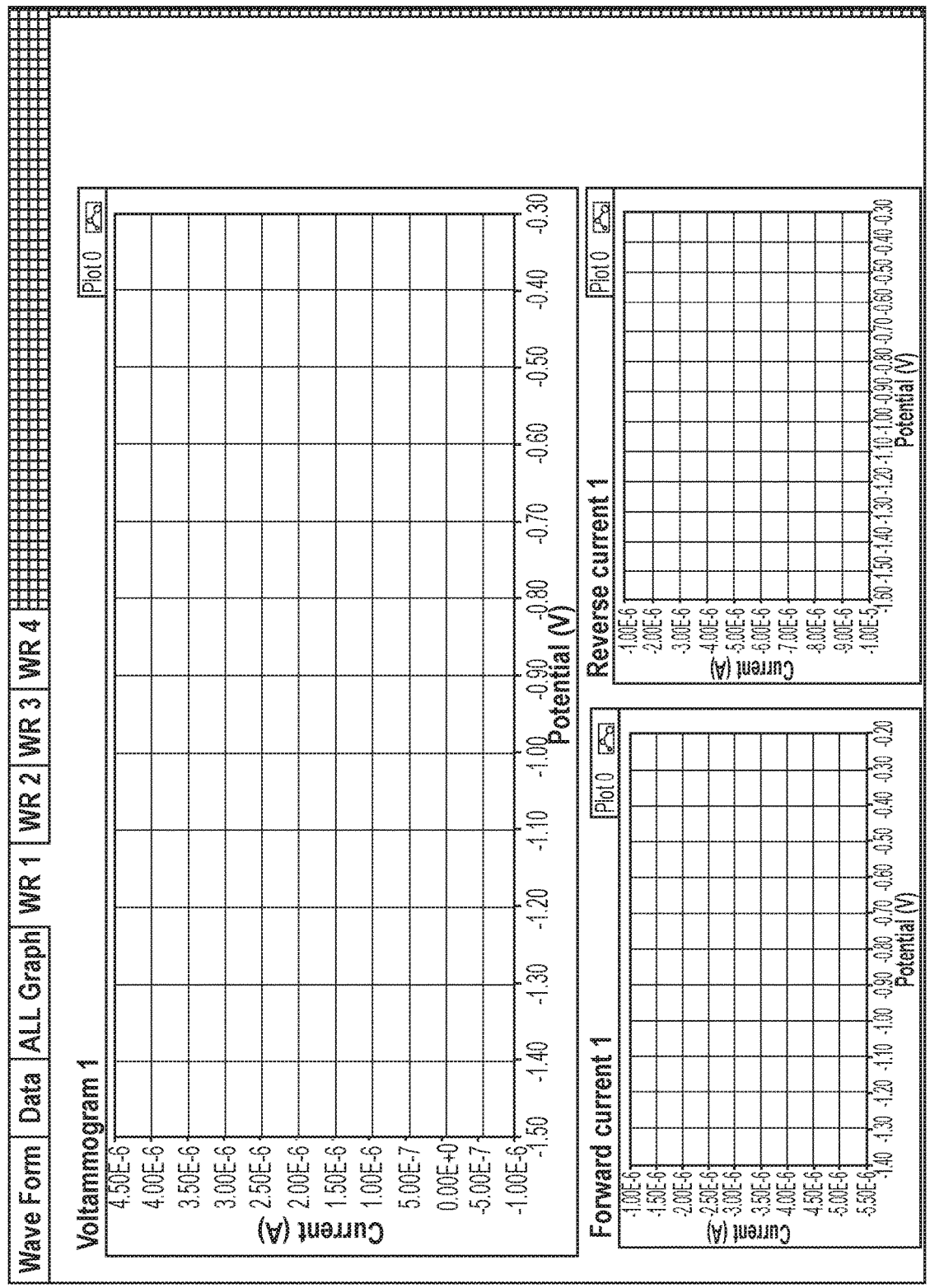
Figure 6D:
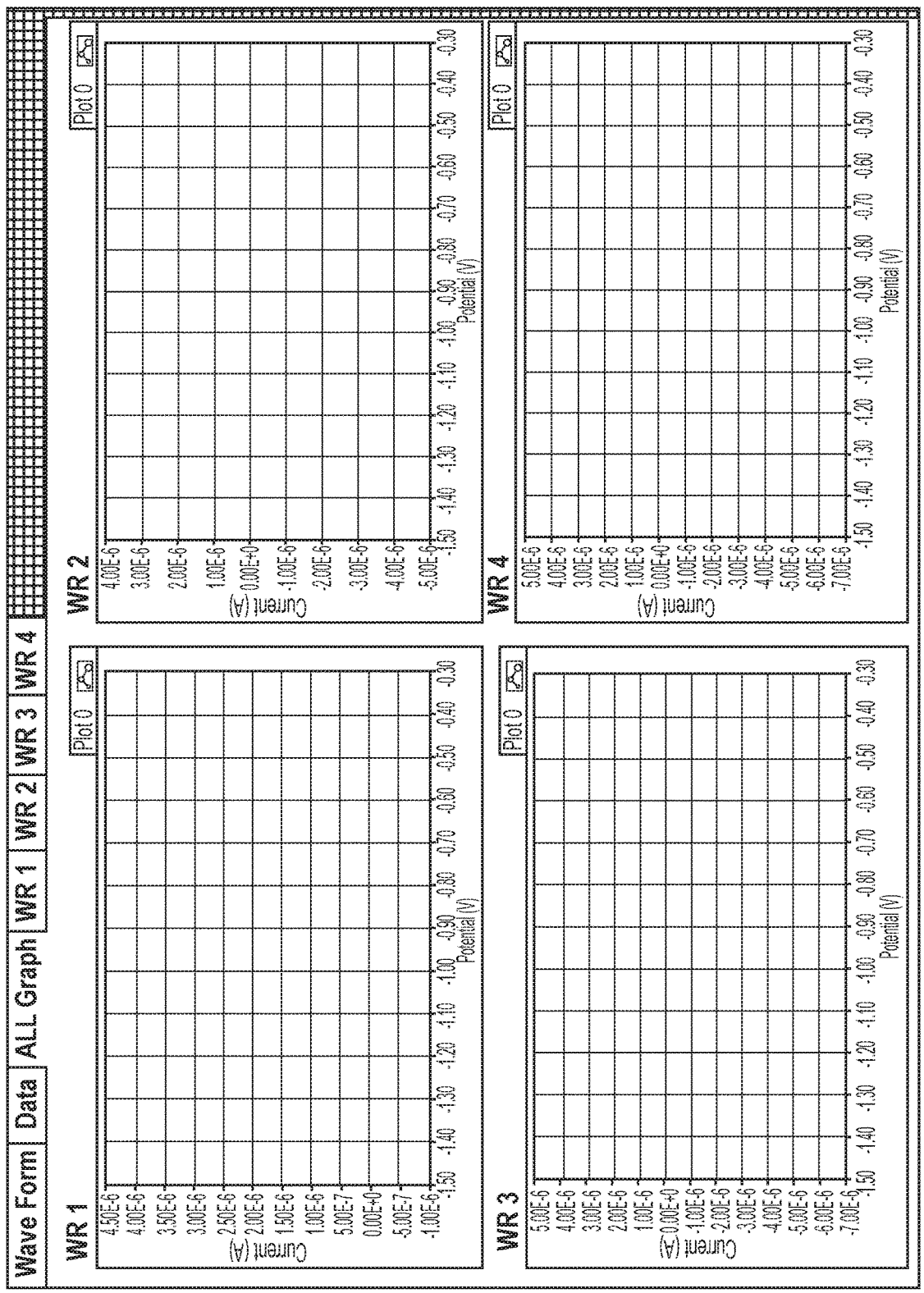

In another embodiment, the invention is a microcontroller-based potentiostat system capable of performing cyclic voltammetry analysis. FIG. 4 shows a block diagram of one embodiment of a potentiostat system of the invention, which consists of a microcontroller, a potentiostat circuit, and level shifters. A MSP430F1611 microcontroller (Texas Instruments, Dallas, Tex., United States), for example, can be used, which is an in-built digital-to-analog converter (D/A converter), analog to digital converter (A/D converter), and universal asynchronous receiver (UART) buffer used for communication between the microcontroller and computer. The microcontroller generates a triangular waveform voltage using 12-bit D/A converter. Since the output voltage is unipolar, an op-amp level shifter circuit is used to make the output voltage bipolar. The level shifted voltage is applied to a potentiostat circuit as shown in FIG. 5.

The potentiostat circuit includes three operational amplifiers (op amp). One (op-amp 1) is used for a current buffer of which the current at the output is capable of providing infinite current. A second op amp (op-amp2) is used for a voltage follower. This results in a voltage difference between the working and reference electrode to be identical as the applied triangular input voltage, generated by the D/A converter. The last op amp (op-amp3) is employed for a current-to-voltage converter, with output voltage proportional to the current between the working and counter electrode. The output voltage corresponding to the current is read by the A/D converter after bipolar output voltage is shifted into unipolar voltage using an additional level shifter.

In one embodiment, a virtual instrument (VI) for data extraction and management employs LabVIEW programming. Two different types of anodic stripping voltammetry having a square and a differential pulse wave form were implemented on the VI. As shown in FIGS. 6A-6D, the VI consists of four tab windows. The waveform parameters of square wave and differential pulse potentials, such as initial, height, increment, and final potentials, can be input on the first tab window (see FIG. 6A). The configuration parameters can be sent to the microcontroller using RS232 communication by pushing a button of 'PM_SET'. Once the MSP430 microcontroller receives the parameters, it generates a sweeping potential between the working electrode and a reference electrode and the resulting current response at the working electrode is measured. Raw data of applied potential and induced currents, including forward and reverse currents at each working electrode, are displayed and graphed on FIG. 6B and FIG. 6C, respectively. The voltammogram of the sensor responses from the four working electrodes were also plotted on FIG. 6D.

In another embodiment using a database of sensor responses obtained by controlling voltage at the working electrode's surface and measuring the induced current (generated by oxidation-reduction processes of electro-active species in solution), correlation of the in situ sensor responses with the database by the method of the invention, and employing an electrochemical tongue of the invention results in both qualitative and quantitative evaluation of analytes in real-time.

Figure 7:
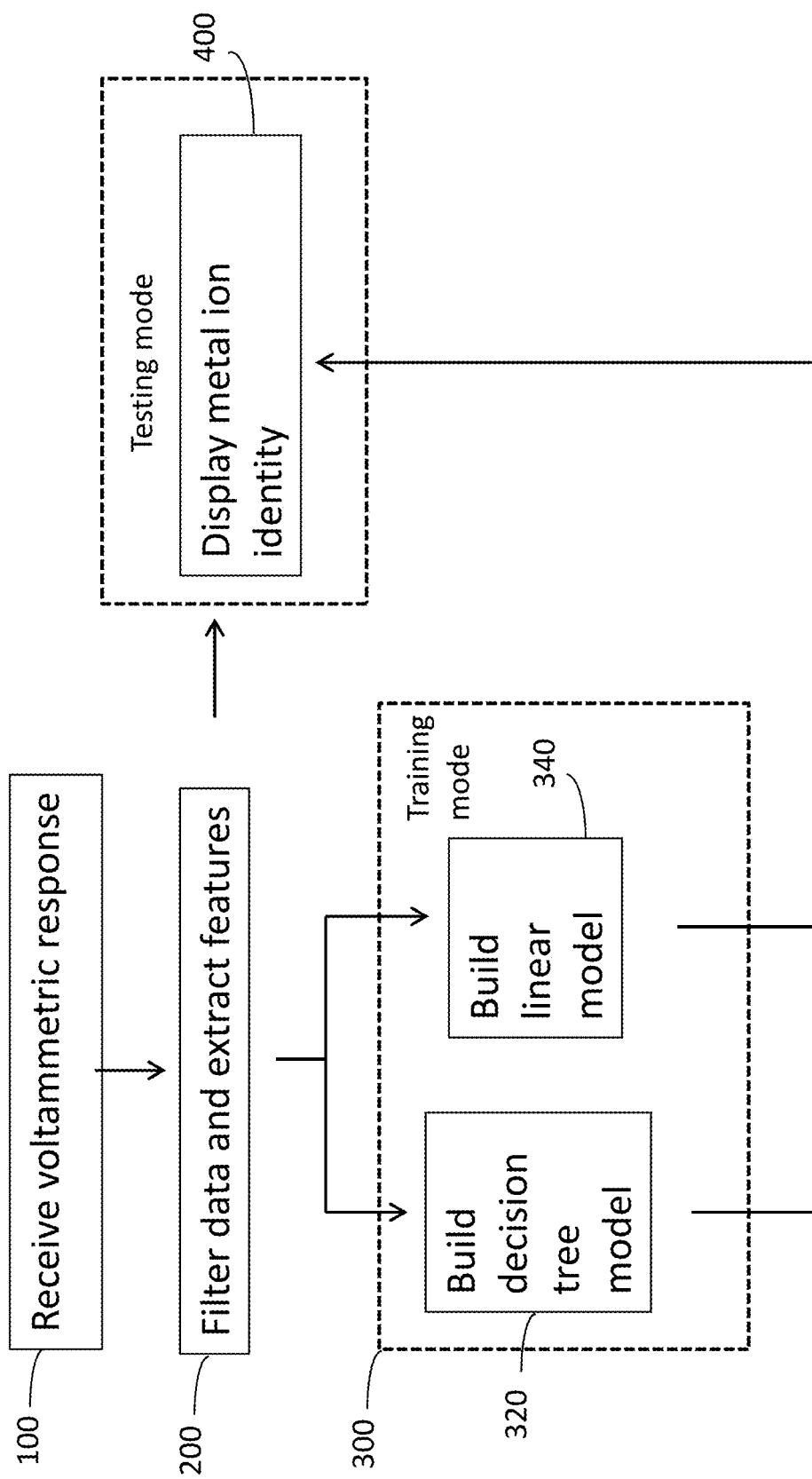
FIG. 7 is a flowchart showing a system for detecting metal ions in a complex mixture.
Figure 34:
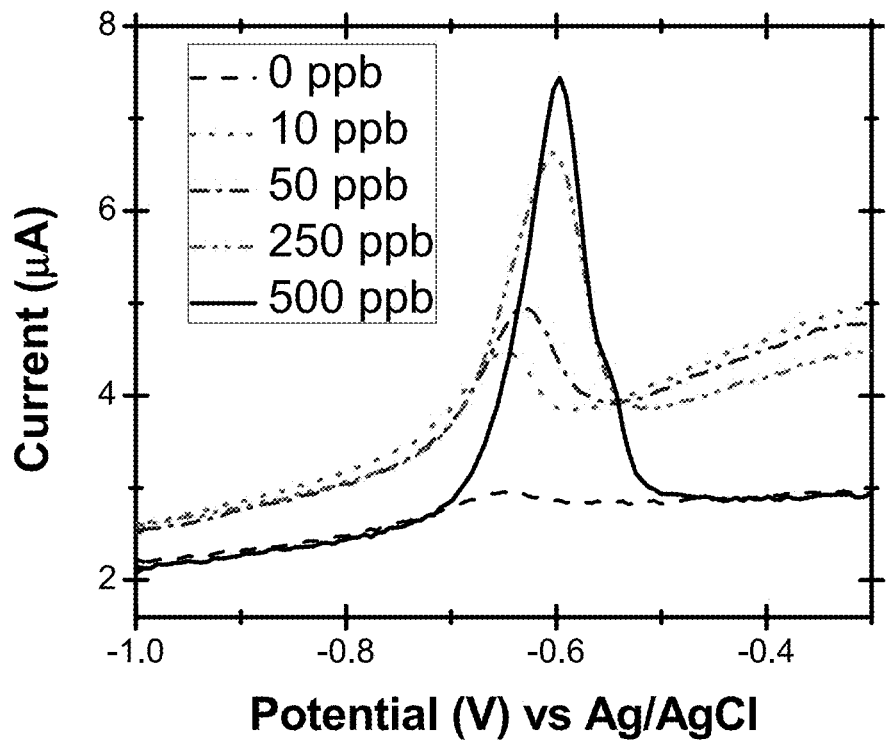
FIG. 34 is a differential pulse stripping voltammogram for different concentrations of $Pb^{2+}$ in 100 mm 2-(N-morpholino)ethanesulfonic acid (MES) buffer (pH 6.5) employing an electrochemical tongue of the invention.

FIG. 7 is a flowchart for an intelligent training and prediction module that can be implemented on a microcontroller unit (MCU). In step 100, the MCU receives a voltammetric response from the working electrode. In step 200, the MCU filters the data and extracts features. The extracted features can be the formal potentials and peak currents from voltammetric responses. For example, the MCU can filter the RAW data using a moving average algorithm (as a smoothing technique) and determine features (peak current and its formal potential) using a peak detection algorithm. The peak detection algorithm can identify peaks by taking the first derivative of the raw sensor response. Among the maximum points, the final peak point can be determined by two user-defined threshold values in terms of the slope of derivative and magnitude of sensor response. Step 300 pertains to a training mode, having substeps 320 and 340. In step 320, a decision tree model is built using the extracted formal potentials. The decision tree has a specific structure (e.g., numbers of nodes and branches). In an initial state of a decision tree, a root node is the first node to which the training set are assigned. If the training sets at the root node consist of two or more classes, a test node is made that will split the training set into two subspaces, or secondary nodes. These can either become terminal nodes, in which a classification is reached, or another test node. The process is repeated until each branch results in a terminal node and a completely discriminating tree is obtained. An exemplary built tree is illustrated in FIG. 34, where terminal nodes represent the labeled heavy metal ions. In step 240, a linear model is built using a Least Square Estimator (LSE), which creates a linear model using the training data (e.g., x-axis: concentrations; y-axis: peak currents). Thus, the MCU can: i) smooth and filter data; ii) identify formal potentials and measure peak currents (or other relevant parameters); and iii) build a decision tree learning and linear model. To reduce noisy signals from raw sensor responses, a moving average algorithm (as a smoothing technique) has been programmed into the MCU. The MCU can also implement a testing mode 400, in which metal ions can be detected in a complex sample. The decision tree and linear model from the training mode 300 are used to predict the identity and concentration of the metal ions. Since the trained decision tree and linear model have critical parameters (e.g., slope and intercept of linear models), the unseen data can determine the identity and concentration of metal ions.

Exemplification

The following are examples of representative embodiments of the invention and are not intended to be limiting in any way.

Example 1 (Prior Art)

Figure 8:
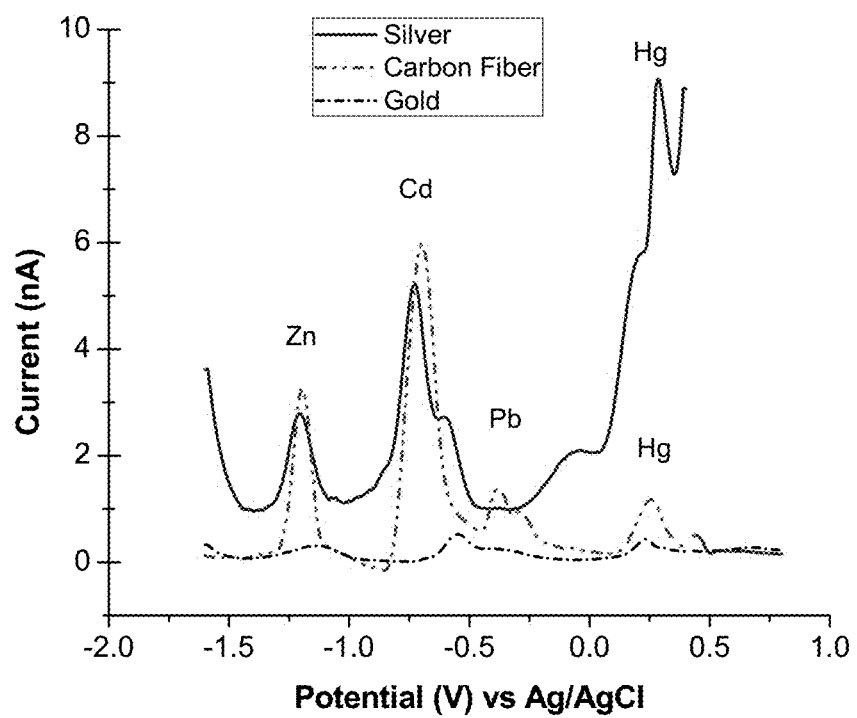
FIG. 8 is a plot of detection of $Zn^{2+}$, $Cd^{2+}$, $Pb^{2+}$, and $Hg^{2+}$ in aqueous samples (at 5 ppm) using a prior art uncoated working electrode.

This example shows the detection of zinc, cadmium, lead, and mercury in water using a multi-sensor array of uncoated microelectrodes. A solution containing 5 ppm of each of $Zn^{2+}$, $Cd^{2+}$, $Pb^{2+}$, and $Hg^{2+}$ was prepared in water. The solution was tested using an array of microelectrodes fitted on a cone penetrometer. Gold, silver, and carbon fiber based microelectrodes were used in this test. As illustrated in FIG. 8, the gold based microelectrode showed good sensitivity towards $Pb^{2+}$ while the response to $Zn^{2+}$ and $Hg^{2+}$ was negligible. The carbon fiber electrode and silver showed good sensitivity to the metal ions in solution.

Example 2 (Prior Art)

Figure 9:
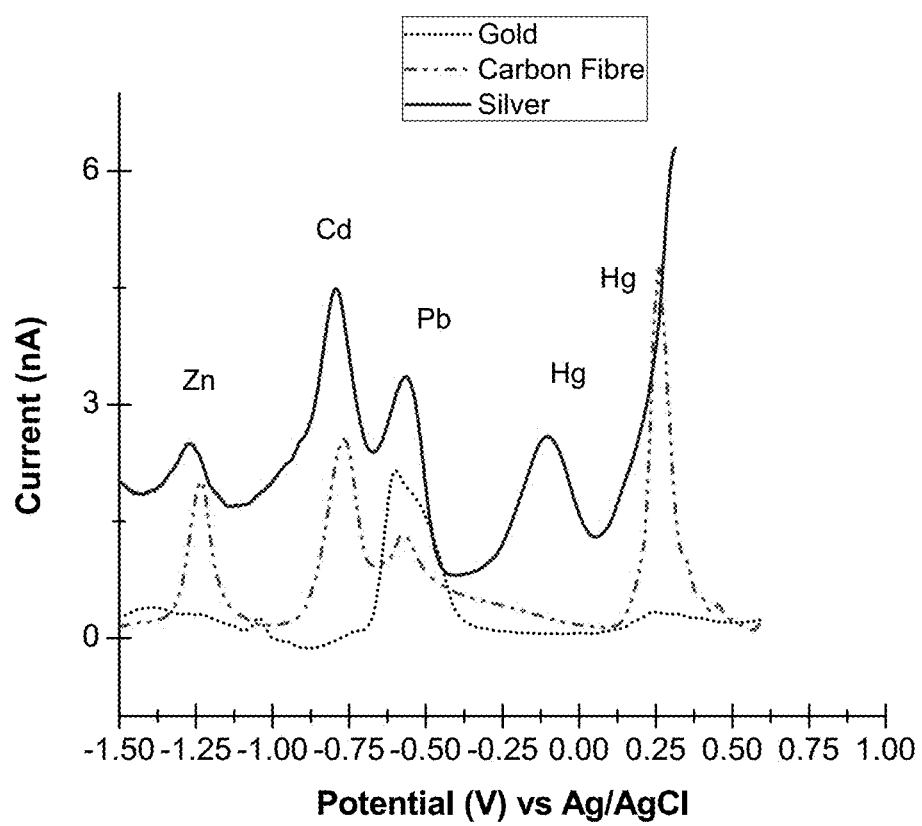
FIG. 9 is a plot of detection of $Zn^{2+}$, $Cd^{2++}$, $Pb^{2+}$, and $Hg^{2+}$ in sand at 5 mg/kg using a prior art uncoated working electrode.

This example shows detection of $Zn^{2+}$, $Cd^{2+}$, $Pb^{2+}$ and $Hg^{2+}$ in sand using a multi-sensor array of microelectrodes. A solution containing 5 mg/kg of each of $Zn^{2+}$, $Cd^{2+}$, $Pb^{2+}$ and $Hg^{2+}$ was prepared in saturated sand. The solution was tested using an array of microelectrodes fitted on a cone penetrometer. Gold, silver and carbon fiber based microelectrodes were used in this test. As illustrated in FIG. 9, the gold based microelectrode showed poor sensitivity towards the metal ions in sand, while the carbon fiber electrode and silver showed good sensitivity to the metal ions. However, in case of the silver microelectrode, prior to the oxidation of mercury a large increase in the back current was observed.

Example 3

This example shows detection of $Cd^{2+}$ in water using a glassy carbon electrode (GCE) having a thiophene-based copolymer coating of one embodiment of the electronic tongue of the invention. The electrode was coated with poly(thiophene-co-n-Pyridin-4-yl-2-thiophen-3-yl-acet-amide) ("PTCPTA") having the following structural formula (V):

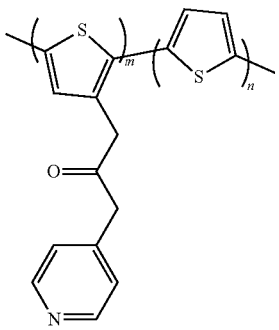

In structural formula (V), m can be an integer from approximately 6 to approximately 100, and n can be an integer from approximately 6 to approximately 100. Preferably, the sum of m+n is at least 10.

Figure 10:
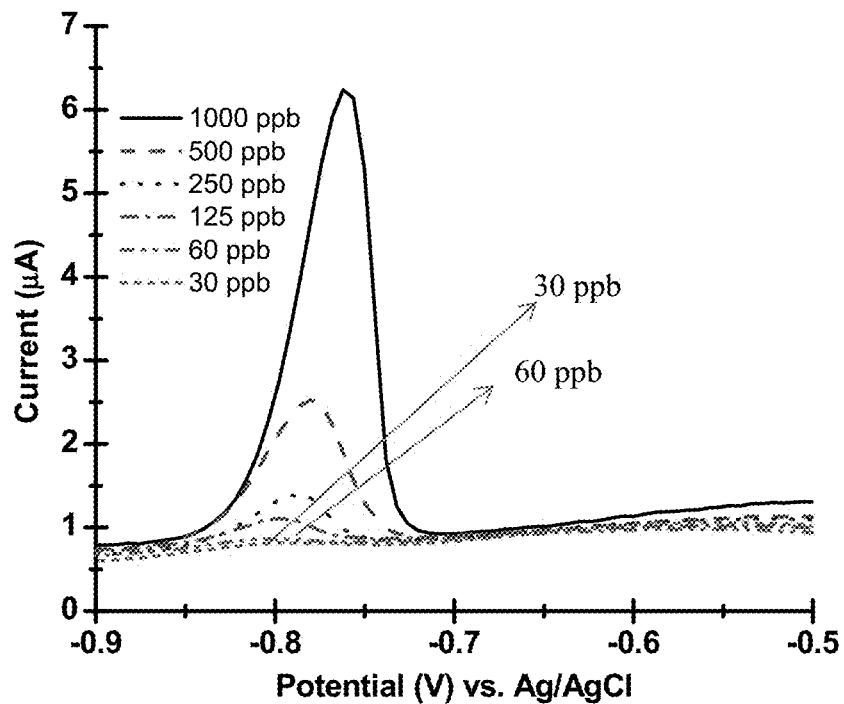
FIG. 10 is a plot of differential pulse stripping voltammograms for $Cd^{2+}$ of various sub-ppm concentrations using one embodiment of a PTCPTA modified glassy carbon electrode.
Figure 11:
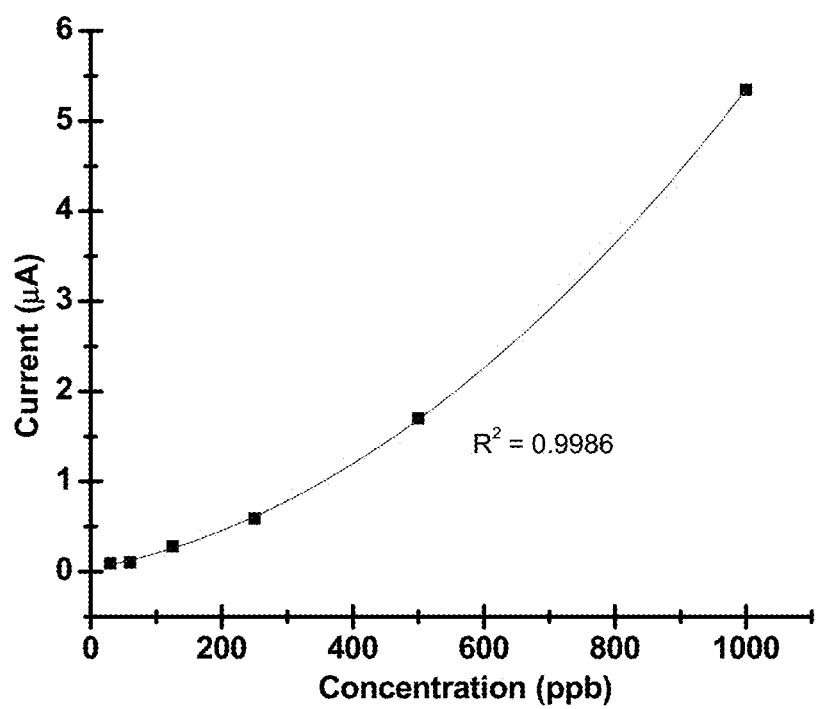
FIG. 11 is a plot of calibration curves for $Cd^{2+}$ obtained using one embodiment polythiophene copolymer modified glassy carbon electrode.

FIG. 10 shows the differential pulse stripping voltammograms of various sub-ppm concentrations of $Cd^{2+}$ in acetate buffer (100 mM, pH 4.5). Results indicate a detection limit of 30 ppb, which is improved level of sensitivity compared to the non-coated membrane. FIG. 11 is a corresponding calibration curve for $Cd^{2+}$ obtained using the polythiophene copolymer modified electrode of the invention.

Example 4

The example shows detection of $Cu^{2+}$ in water using a polyphenol-modified glassy carbon electrode of an electrochemical tongue of one embodiment of the invention. The electrode was coated with polymer having the following structural formula, where n can be an integer from approximately 6 to approximately 100:

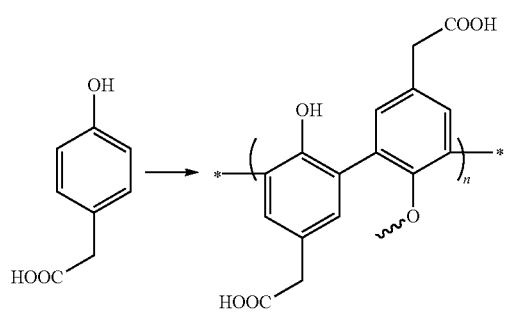

Figure 12:
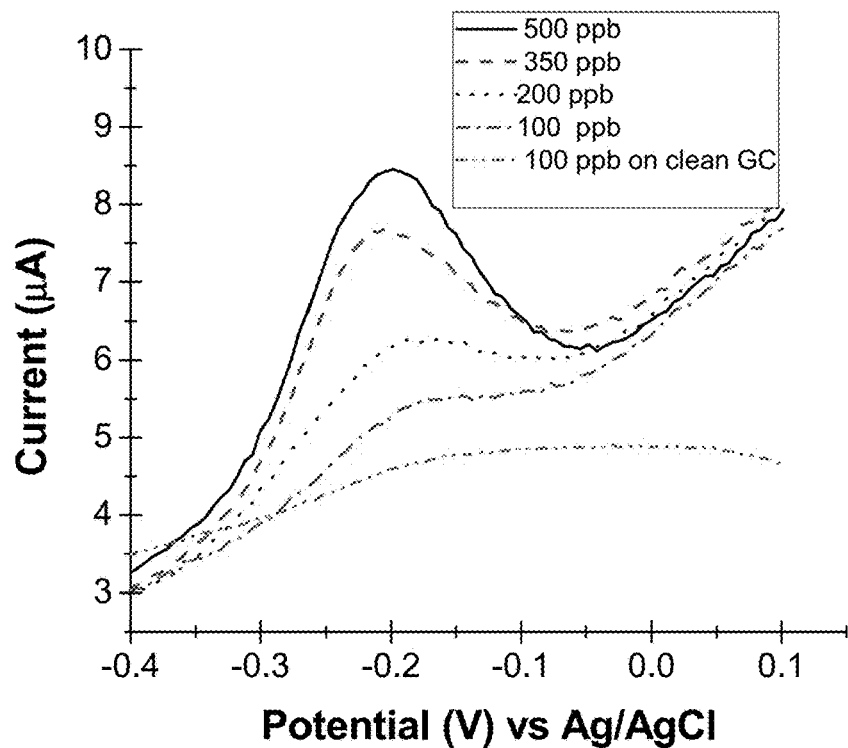
FIG. 12 is a series of differential pulse stripping voltammograms for various sub-ppm concentrations of $Cu^{2+}$ using a poly(hydroxyl phenyl acetic acid) modified glassy carbon electrode of one embodiment of the electrochemical tongue of the invention in aqueous solutions.
Figure 13:
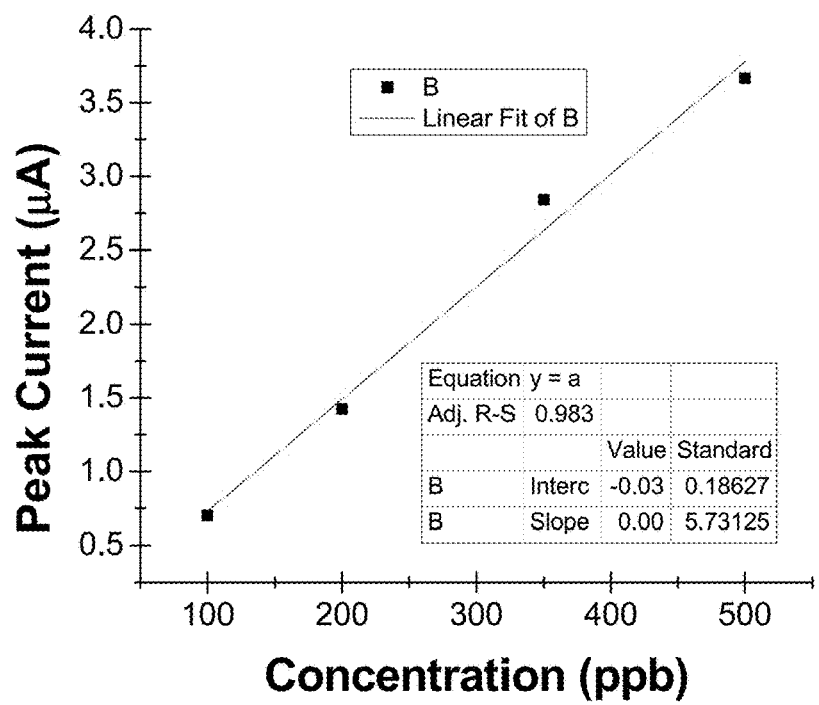
FIG. 13 is a calibration curve for various sub-ppm concentrations of $Cu^{2+}$ using a poly(hydroxyl phenyl acetic acid) modified glassy carbon electrode of an embodiment of the electrochemical tongue of the invention in aqueous solutions.

The poly(hydroxyl phenyl acetic acid) modified glassy carbon electrode was used for the detection of $Cu^{2+}$ in aqueous solutions. The differential pulse stripping voltammograms (DPSV) for different concentrations of $Cu^{2+}$ in a 50 mM phosphate buffer are shown below in FIG. 12. The poly(hydroxyl phenyl acetic acid) modified GCE is capable of detecting concentrations as low as 100 ppb of $Cu^{2+}$. A calibration curve was also prepared, shown in FIG. 13.

Example 5

Figure 14:
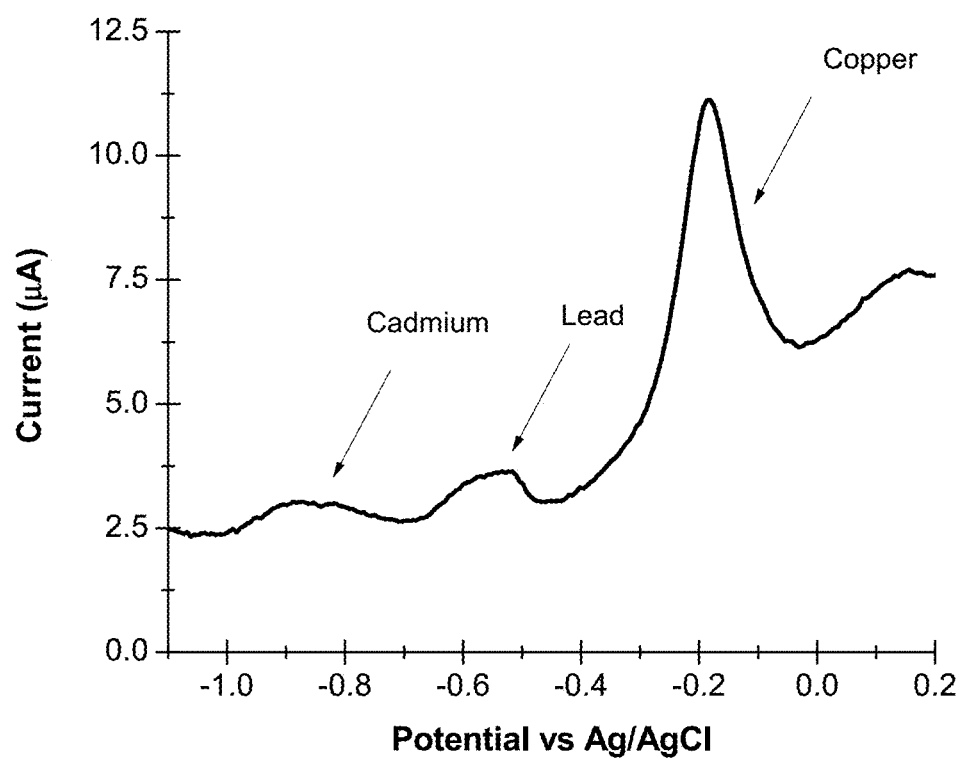
FIG. 14 is a plot of simultaneous detection of $Cd^{2+}$, $Pb^{2+}$, and $Cu^{2+}$ in aqueous samples at 500 ppb using a poly(hydroxyl phenyl acetic acid) modified glassy carbon electrode of an embodiment of the electrochemical tongue.

This example shows simultaneous detection of $Cd^{2+}$, $Pb^{2+}$, and $Cu^{2+}$ in water using a poly(hydroxyl phenyl acetic acid) of another embodiment of a modified glassy carbon electrode (GCE) of an electronic tongue of the invention. A solution containing 500 ppb of $Cd^{2+}$, $Pb^{2+}$, and $Cu^{2+}$ in 50 mM phosphate buffer was prepared and tested using the poly(hydroxyl phenyl acetic acid) modified GCE. As illustrated in FIG. 14, the polymer modified electrode can detect all three metals with good sensitivity. The sensor demonstrated greater sensitivity to $Cu^{2+}$ than the other metal ions.

Example 6

Figure 15:
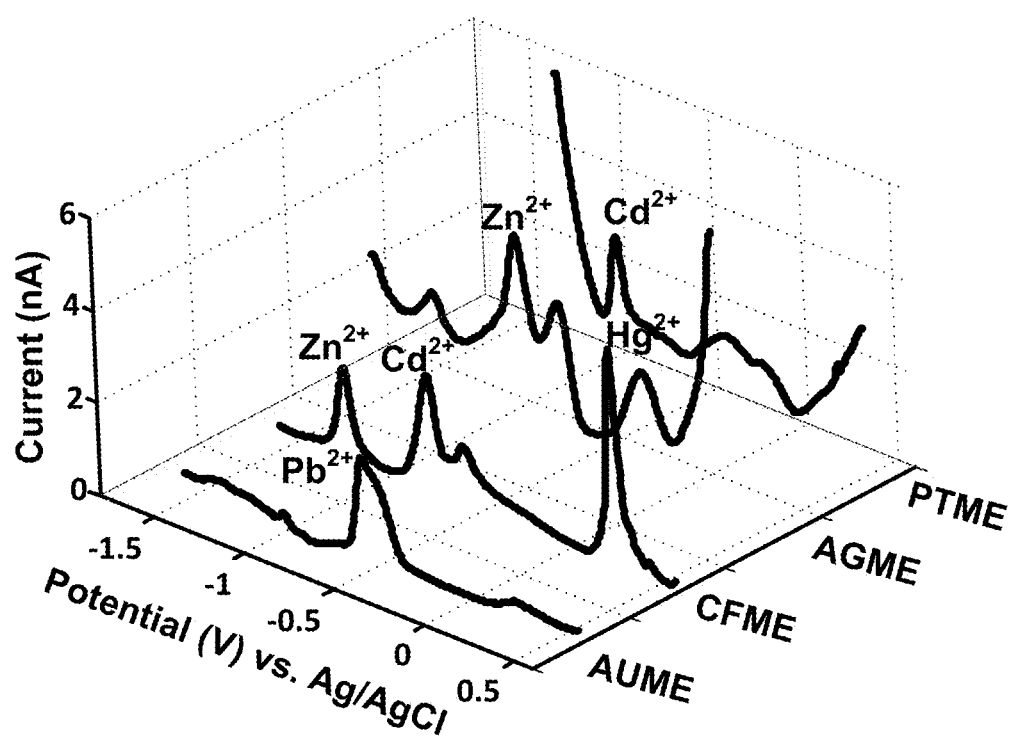
FIG. 15 is a plot of multi-electrode responses to $Zn^{2-}$, $Cd^{2-}$, $Pb^{2+}$, and $Hg^{2+}$ in water employing an electrochemical tongue.

This example illustrates electrode sensitivity toward a multitude of target metal ions. FIG. 15 illustrates the variation in sensor response to an aqueous solution containing $Zn^{2+}$, $Cd^{2+}$, $Pb^{2+}$, $Pb^{2+}$, and $Hg^{2+}$. In FIG. 15, AUME refers to gold microelectrode; CFME refers to carbon fiber microelectrode; AGME refers to silver microelectrode; PTME refers to platinum microelectrode. While CFME displayed well-defined peak currents due to the presence of all four target ions, $Pb^{2+}$ was primarily dominant at the AUME. Additionally, the oxidation of solid metal substrates of the PTME and AGME hindered responses from highly cathodic/anodic ions (i.e., $Zn^{2+}$ and $Hg^{2+}$, respectively) yielding a narrow potential window for detecting $Pb^{2+}$ and $Cd^{2+}$. The solid metal electrodes (AUME, PTME, and AGME) were also found to be selective towards dissolved oxygen, which was highly valuable for determining influences of DO levels on peak current responses of target ions.

Example 7

Figure 16:
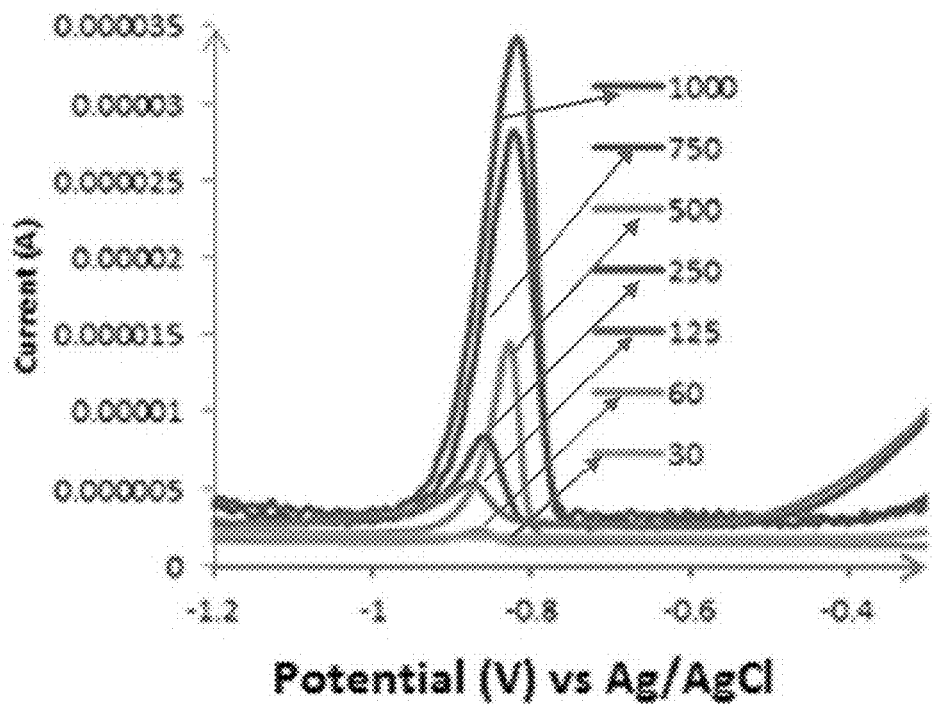
FIG. 16 is a differential pulse stripping voltammogram of $Cd^{2+}$ at varying concentrations using a PTAA-coated glassy carbon electrode of an electrochemical tongue of the invention.
Figure 17:
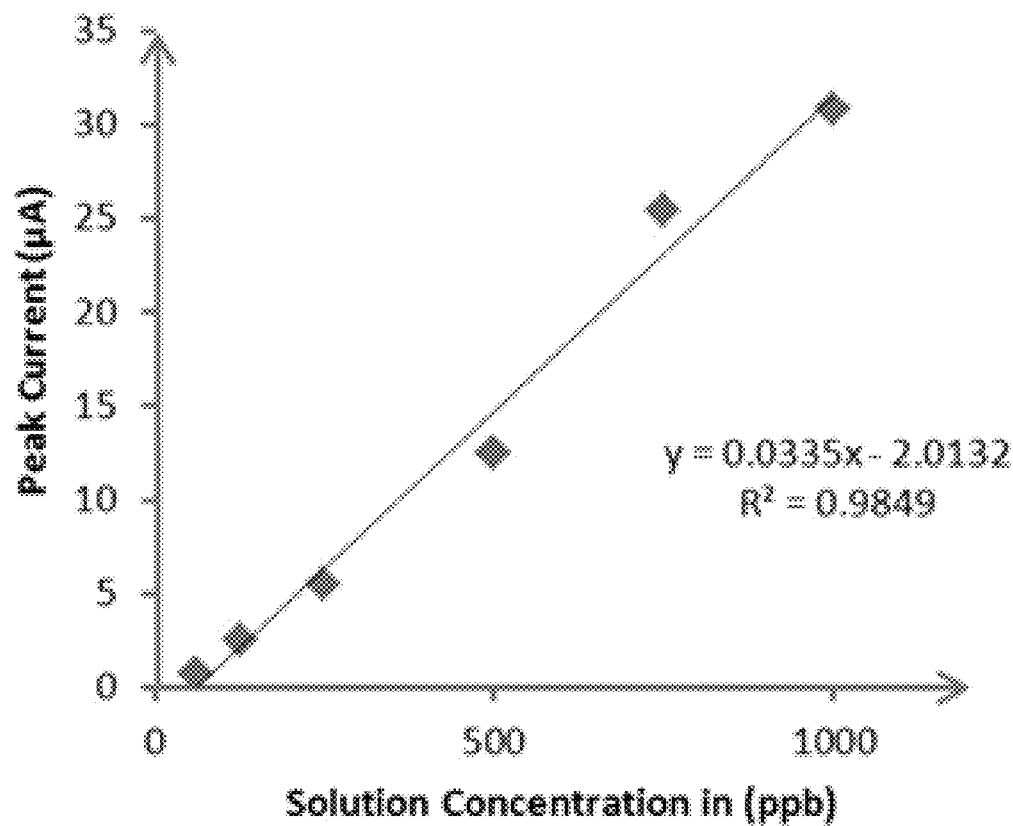
FIG. 17 is a calibration curve for $Cd^{2+}$ using a PTAA-coated glassy carbon electrode of an electrochemical tongue of the invention.

This example illustrates an electrode coated with poly(thiophene acetic acid) (PTAA). FIG. 16 is a DPSV for $Cd^{2+}$ of varying concentrations using a PTAA modified GCE, and FIG. 17 is a calibration curve for $Cd^{2+}$ using the PTAA modified electrode. As FIG. 16 illustrates, the polymer coated electrode demonstrated a level of detection in the parts-per-billion range.

Example 8

This example demonstrates an electrode coated with a polyphenol. The phenol monomer is 4-hydroxyphenylacetic acid (HPA), which has the following structure (IV):

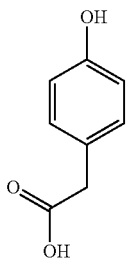 [SMILES: O=C(O)Cc1ccc(O)cc1]

The phenolic monomer was electrochemically polymerized on a GCE by potential cycling (CV) a 2.5 mM solution of monomer dissolved in 50 mM perchloric acid between −0.7 and 1.25 V for 100 cycles.

All tests were performed in 5 ml solutions of metal salts (lead nitrate, cadmium chloride, and copper (II) chloride) prepared in phosphate buffer (pH 6.5, buffer strength 50 mM). DPSV techniques were performed subsequent to metal ion deposition at −1.5 V (vs. Ag/AgCl) for 300 seconds. Differential pulse parameters used include a 75 mV pulse height, 100 ms pulse width, and a 750 ms period with a 6 mV step increment. Each pulse was swept between −1.5 and 0.1 V vs. Ag/AgCl.

Figure 18:
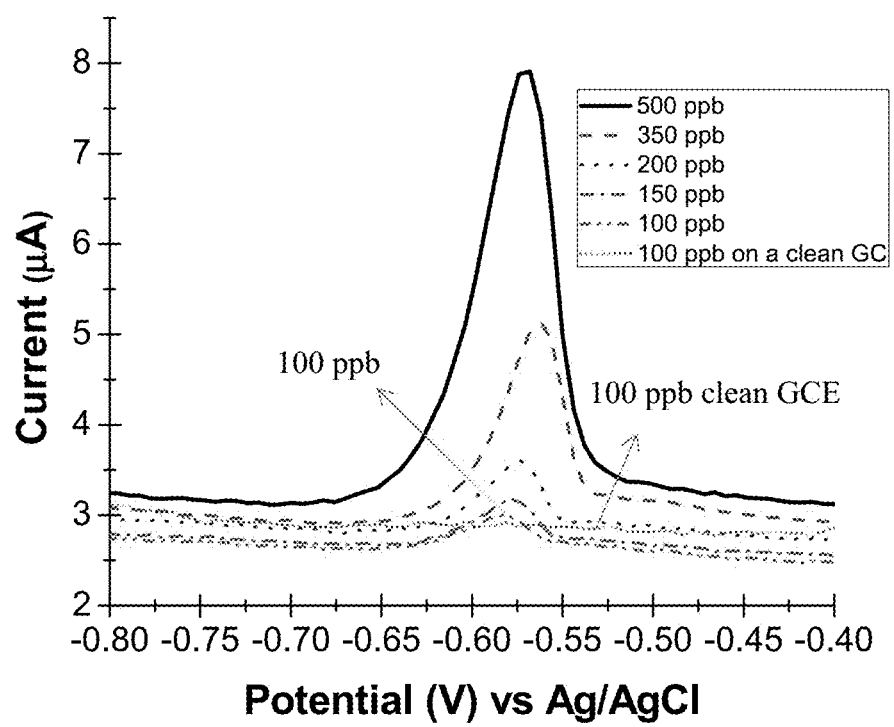
FIG. 18 is a differential pulse stripping voltammogram of $Pb^{2+}$ at varying concentrations using a poly(HPA)-coated glassy carbon electrode of an electrochemical tongue of the invention.
Figure 19:
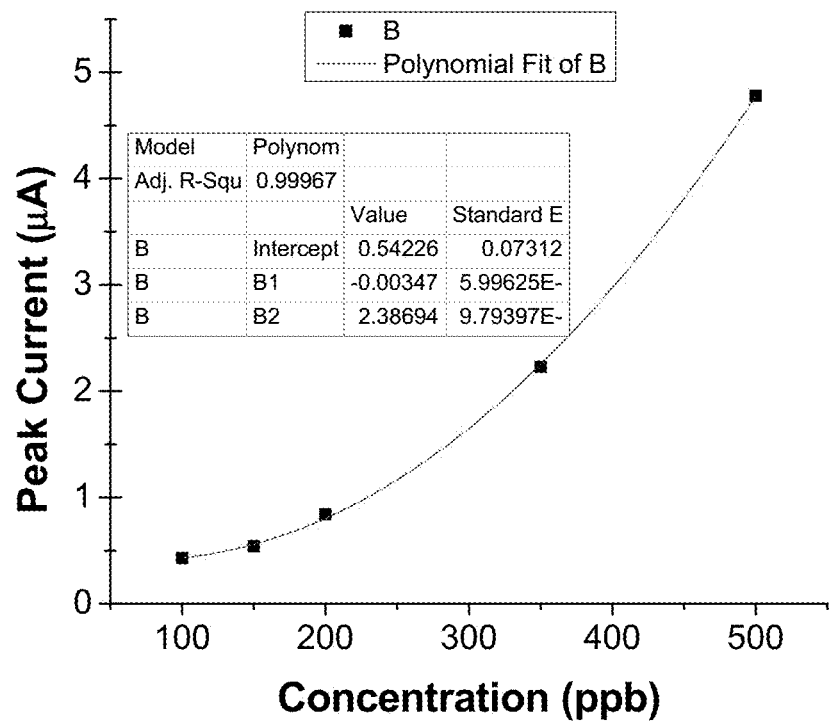
FIG. 19 is a calibration curve for $Pb^{2+}$ using a poly(HPA)-coated glassy carbon electrode of an electrochemical tongue of the invention.

FIG. 18 shows the DPSV for different concentrations of $Pb^{2+}$, and FIG. 19 shows a corresponding calibration curve. As shown in FIG. 18, the poly(HPA) coated GCE can detect concentrations down to 100 ppb of $Pb^{2+}$.

Figure 20:
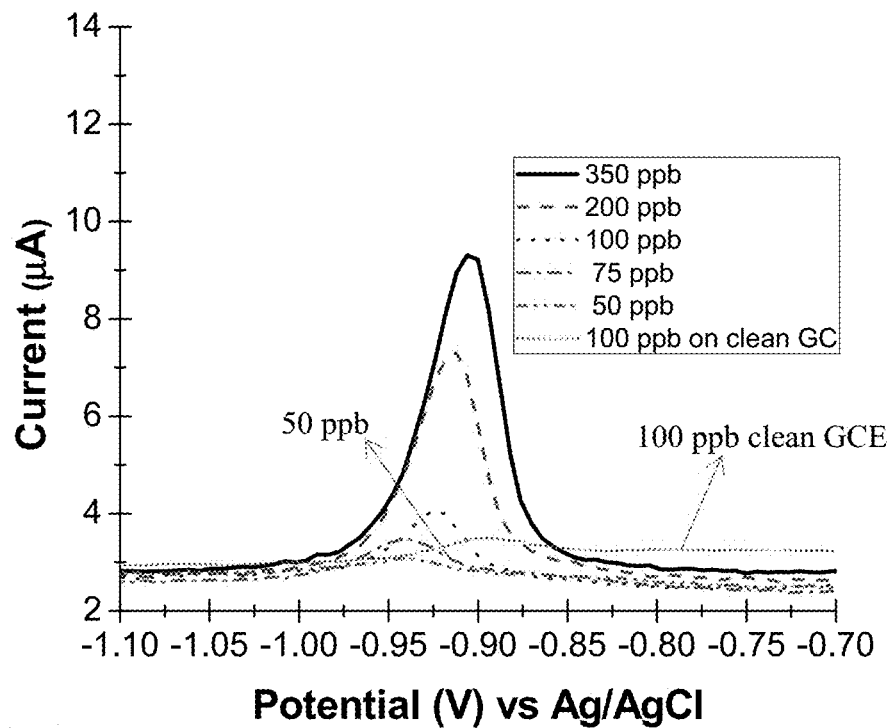
FIG. 20 is a differential pulse stripping voltammogram of $Cd^{2+}$ at varying concentrations using a poly(HPA)-coated glassy carbon electrode of an electrochemical tongue of the invention.
Figure 21:
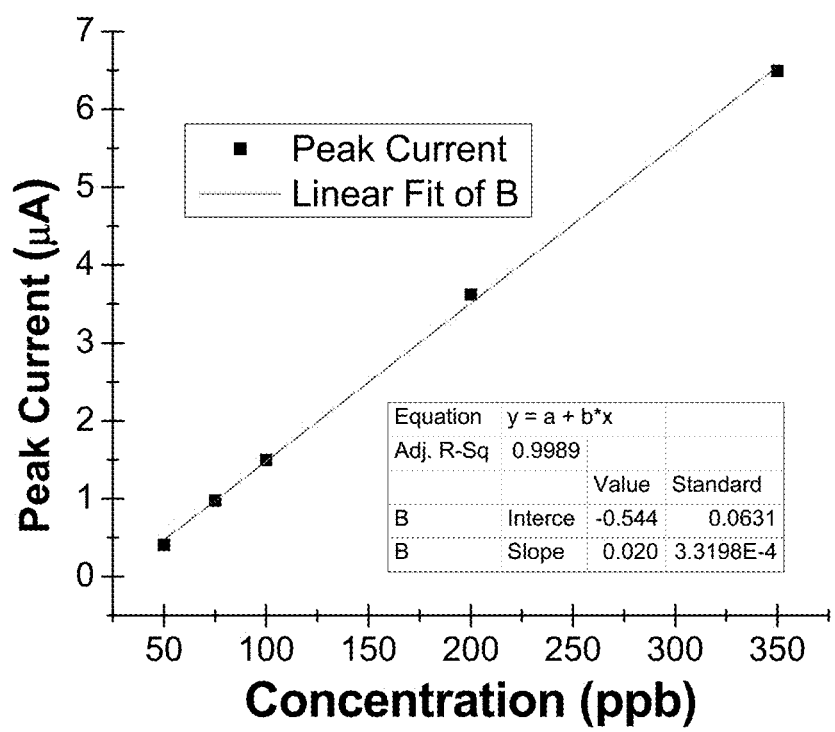
FIG. 21 is a calibration curve for $Cd^{2+}$ using a poly(HPA)-coated glassy carbon electrode of an electrochemical tongue of the invention.

FIG. 20 shows the DPSV for different concentrations of $Cd^{2+}$, and FIG. 21 shows a corresponding calibration curve. As shown in FIG. 20, the poly(HPA) coated GCE can detect concentrations down to 50 ppb of $Cd^{2+}$.

Figure 22:
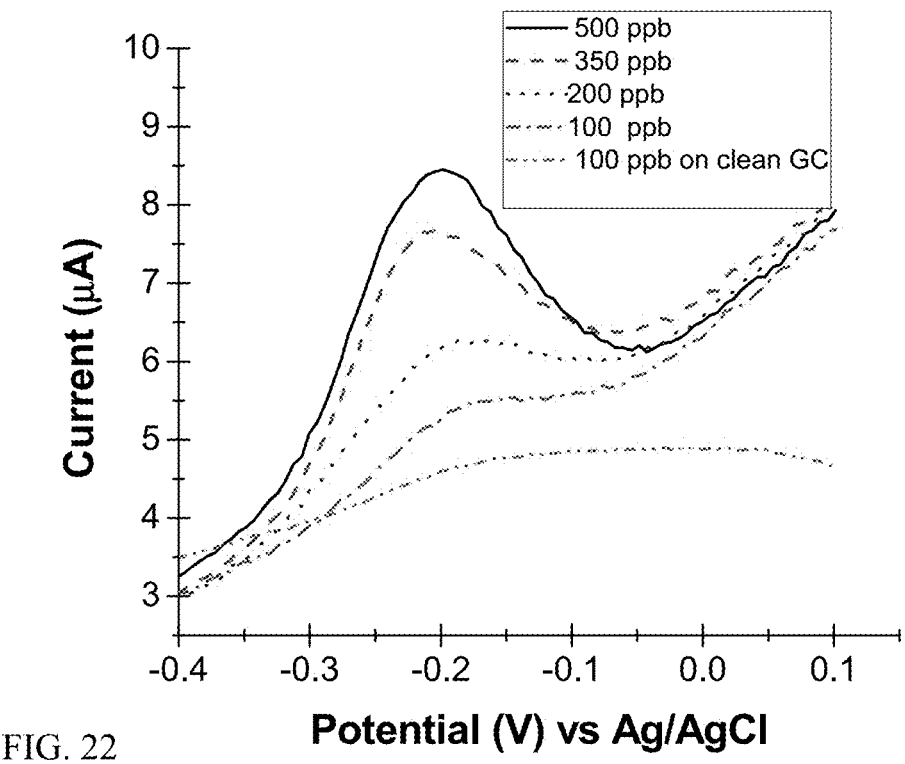
FIG. 22 is a differential pulse stripping voltammogram of $Cu^{2+}$ at varying concentrations using a poly(HPA)-coated glassy carbon electrode of an electrochemical tongue of the invention.
Figure 23:
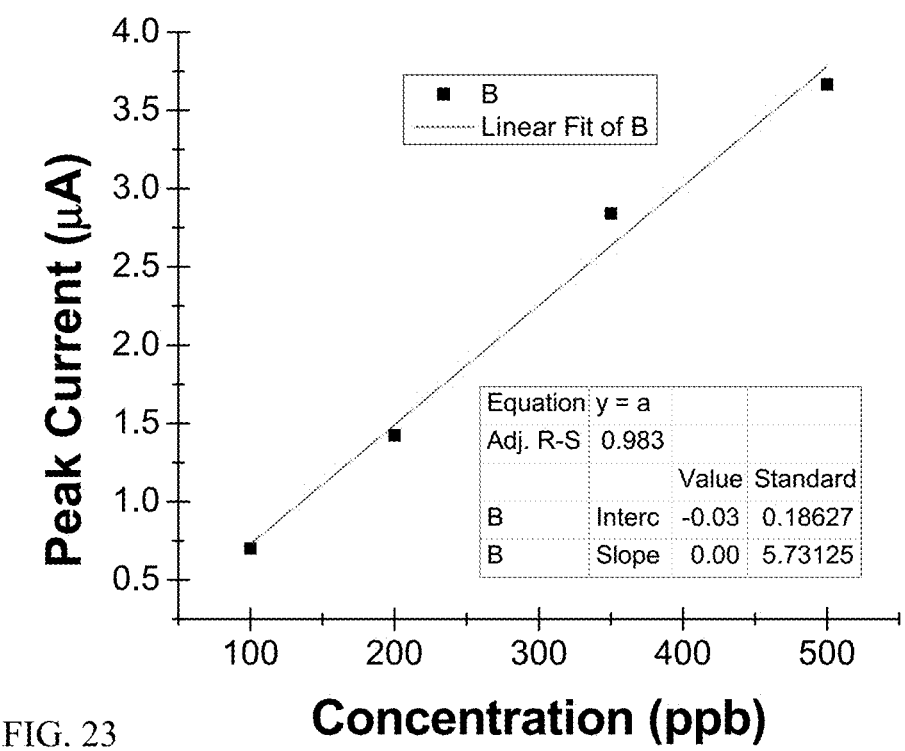
FIG. 23 is a calibration curve for $Cu^{2+}$ using a poly(HPA)-coated glassy carbon electrode of an electrochemical tongue of the invention.

FIG. 22 shows the DPSV for different concentrations of $Cu^{2+}$, and FIG. 23 shows a corresponding calibration curve. As shown in FIG. 22, the poly(HPA) coated GCE can detect concentrations down to 100 ppb of $Cu^{2+}$.

The response of the poly(HPA) coated GCE was compared to a clean GCE to confirm the improvement in the level of detection of $Pb^{2+}$, $Cd^{2+}$, and $Cu^{2+}$, as shown in Table 1.

TABLE 1

| Metal Ion (100 ppb concentration) | Peak Current Response on Clean GCE (μA) | Peak Current Response on poly(HPA) modified clean GCE (μA) |
|---|---|---|
| Lead | No response | 0.265 |
| Cadmium | 0.345 | 1.495 |
| Copper | No response | 0.705 |

Figure 24:
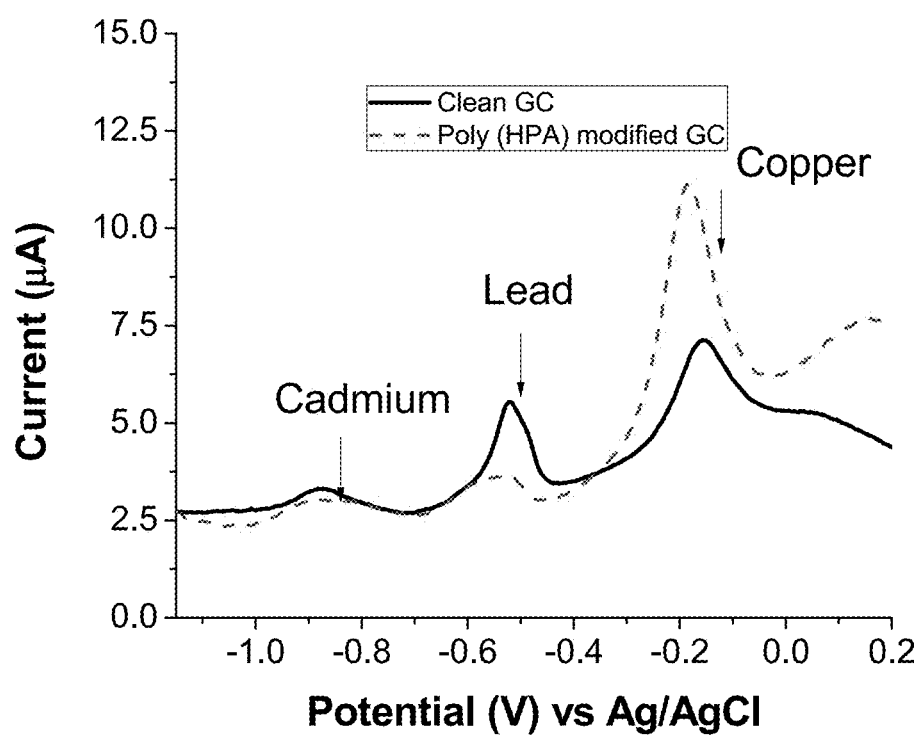
FIG. 24 is a comparison of the response to simultaneous detection of 500 ppb of $Cd^{2+}$, $Pb^{2+}$, and $Cu^{2+}$ employing a electrochemical tongue of the invention.
Figures 25, 26, 27, 28:
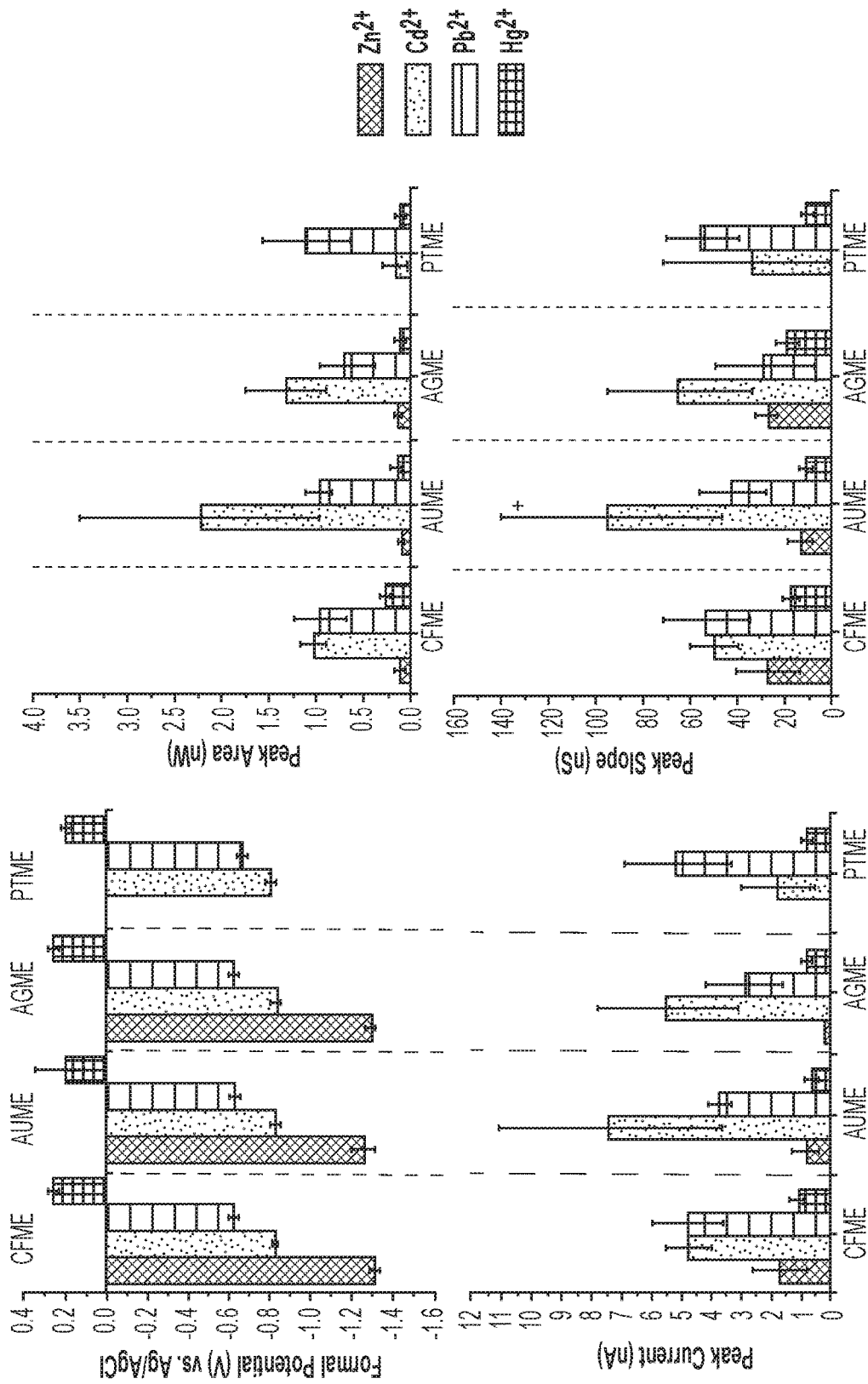
FIG. 25 is the observed formal potential for sensor responses for $Zn^{2+}$, $Cd^{2+}$, and $HG^{2}+$ at four different types of electrodes.
FIG. 26 is the peak areas for the four different types of electrodes represented in FIG. 25.
FIG. 27 is the peak currents for the four different types of electrodes represented in FIG. 25.
FIG. 28 is the peak slopes for the four different types of electrodes represented in FIG. 25.

The poly(HPA) coated GCE was tested in a complex solution containing $Pb^{2+}$, $Cd^{2+}$, and $Cu^{2+}$ and compared the an uncoated GCE in the same solution. As show in FIG. 24, the poly(HPA) modified shows superior sensitivity for $Cu^{2+}$.

Example 9

This example demonstrates the response generated by four different microelectrodes for four metal ions (in separate solutions), each at five concentrations, with a total of five iterations for each. Parameters extracted to establish quantitative and qualitative analysis include peak currents, peak areas, slope of responses induced through the onset of oxidation, and observed formal potentials. FIGS. 25-28 show the results of these parameters for 10 ppm $Zn^{2+}$, $Cd^{2+}$, $Pb^{2+}$, and $Hg^{2+}$. No responses to $Zn^{2+}$ were observed at the PTME due to high back currents (inherent in the formation of hydronium ions during electrolysis) evident at highly cathodic potentials, which masked responses from the target ion.

Figure 29:
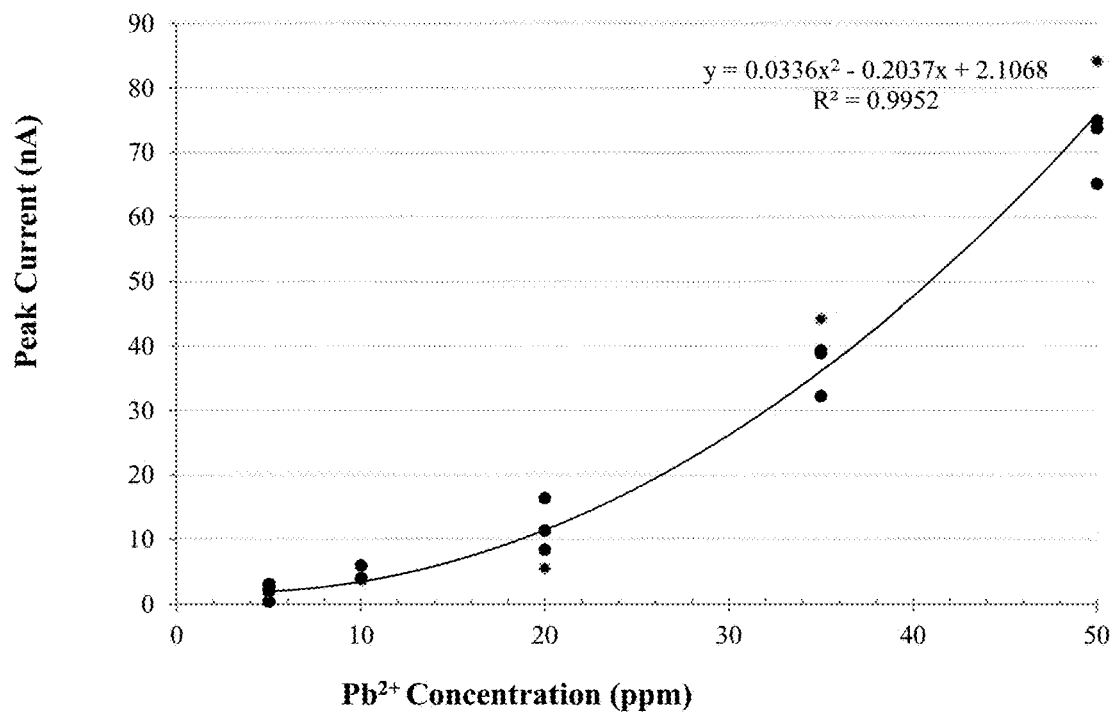
FIG. 29 is a calibration plot for $Pb^{2+}$ using an uncoated carbon fiber microelectrode.
Figure 30:
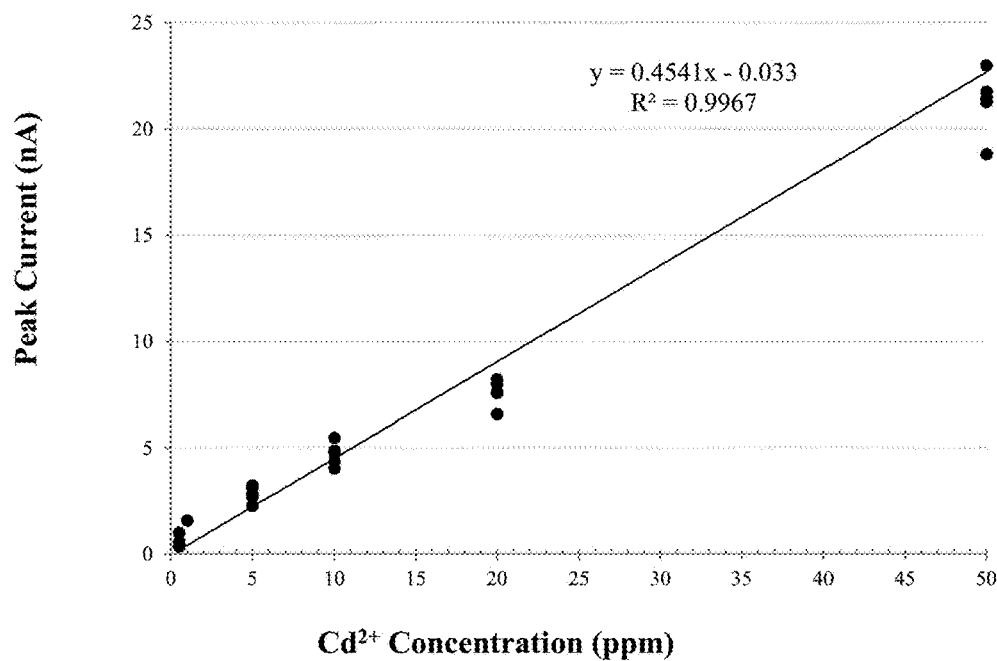
FIG. 30 is a calibration plot for $Cd^{2+}$ using an uncoated carbon fiber microelectrode.

Error bars in FIGS. 25-28 display the variability in sensor responses over the five iterations. The magnitudes of peak currents were dominant for both $Cd^{2+}$ and $Pb^{2+}$, but greater ranges in responses were also evident. This was attributed to the low ionic strength of solutions, as well as the close proximity (considering Formal Potentials) to DO. To further outline variance between iterations, two calibration plots (peak currents versus target ion concentration) are shown in FIGS. 29 and 30 for $Pb^{2+}$ and $Cd^{2+}$, respectively, at a CFME.

Figure 31:
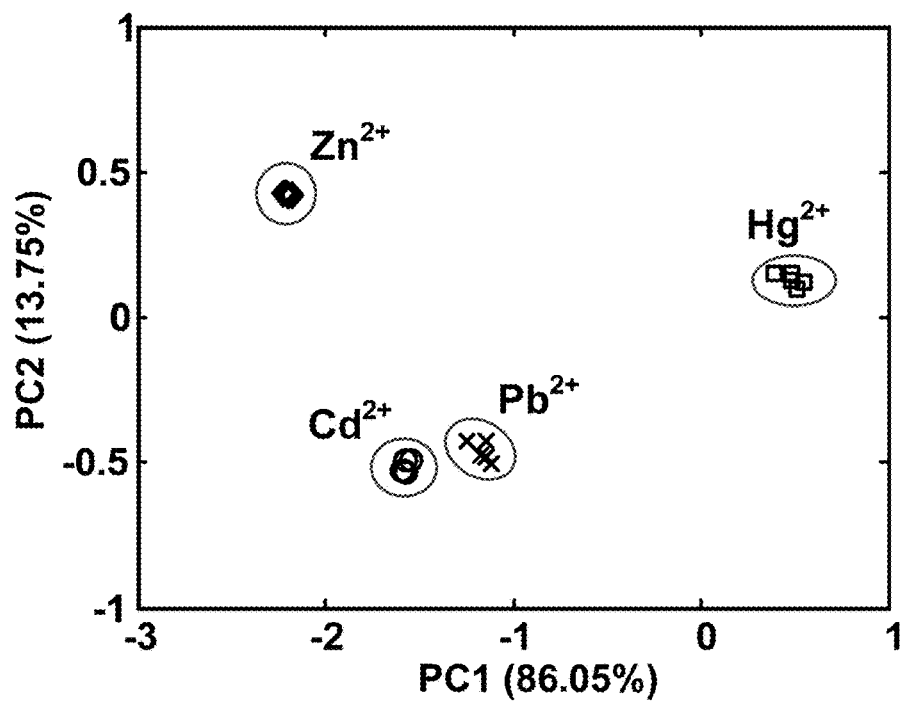
FIG. 31 is a plot showing principal component analysis (PCA) employing an electrochemical tongue of the invention.
Figure 32:
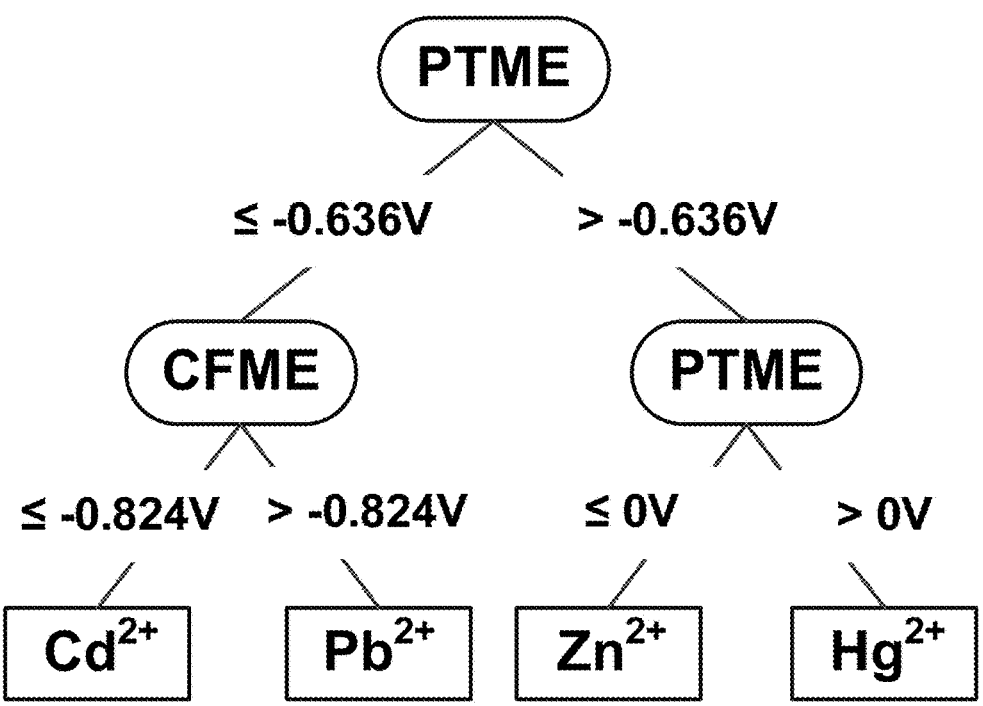
FIG. 32 is a decision tree model generated for classification.

To overcome the variability between iterations, machine learning techniques, such as are known in the art, were implemented. Both Principal Component Analysis (PCA) and a decision tree were used to analyze the results, as shown in FIGS. 31 and 32, respectively. PCA results showed well separated clusters of each heavy metal and 99.8% of the sample variance was captured by the first two principal components. Well separated clusters in the Principal Component Analysis indicates that the system can be trained to accurately classify ions. If the clusters in the PCA plot overlap, another type of electrode could be used to more clearly differentiate the overlapping clusters. The decision tree can classify the ions accurately using responses from just the PTME and CFME electrodes, though more can be used.

Example 10

Figure 33:
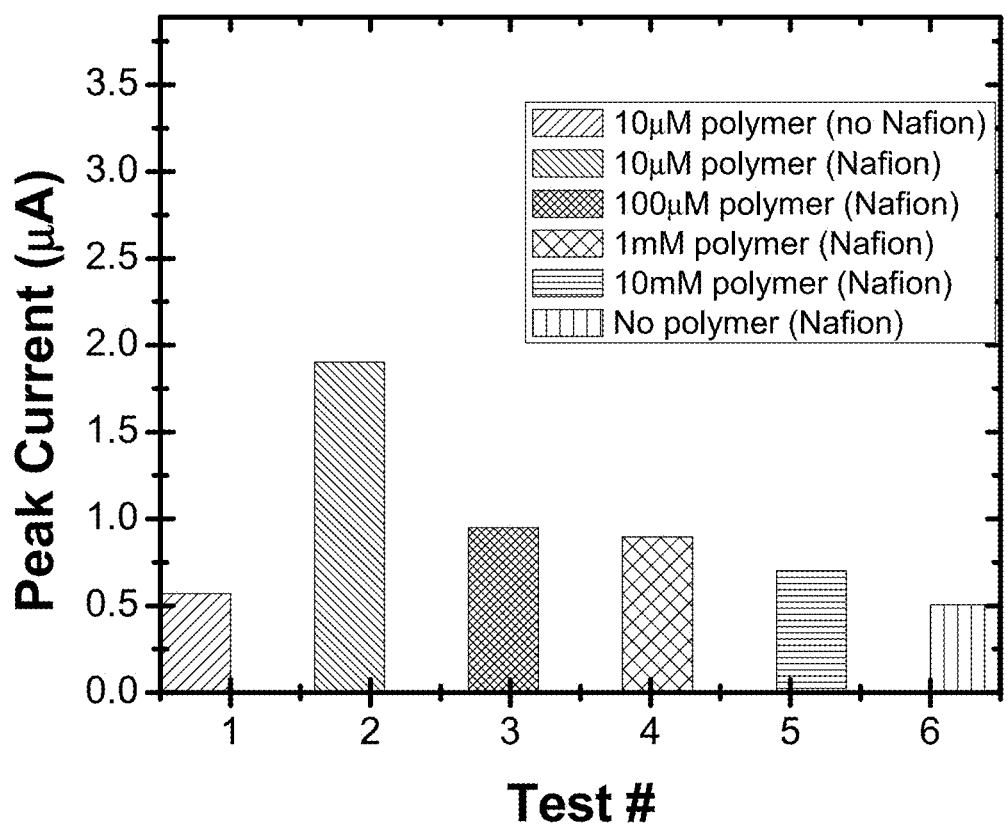
FIG. 33 shows the response of a poly-HPA coated glassy carbon electrode of the invention that has been overcoated with NAFION to 100 ppb $Pb^{2+}$.

This example demonstrates that the robustness of the polymer film can be improved by over-coating. Chemically synthesized poly(hydroxyl phenyl acetic acid) was dissolved in a solution of ammonium hydroxide. Solutions of varying concentration of polymer were prepared. 10 μL of the polymer solution was drop cast on the surface of a glassy carbon electrode. The solvent was then evaporated in order to obtain a cast film of the polymer. Approximately 2 μL of a Nafion solution in methanol was cast onto the surface of the polymer modified electrode to improve the robustness of the coating. The response of the polymer coated electrodes containing varying polymer concentration to 100 ppb $Pb^{2+}$ was compared in order identify an optimal concentration of the polymer needed to improve the sensitivity of the sensor. A comparison of the sensor response of the polymer coated electrodes of varying coating thickness to 100 ppb of $Pb^{2+}$ is shown in the FIG. 33. While this example demonstrates overcoating with NAFION, one of ordinary skill in the art will understand that the overcoating can be any suitable conductive fluoropolymer.

Example 11

Figure 35:
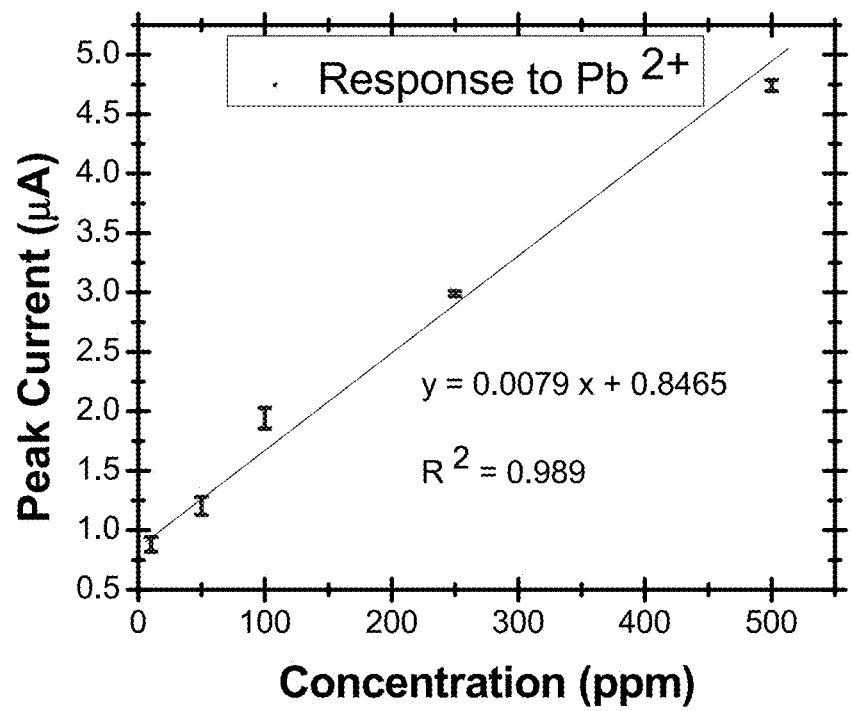
FIG. 35 is a calibration curve for $Pb^{2+}$ using the electrochemical tongue employed to generate the differential pulse stripping voltammogram of FIG. 34.

This example demonstrates detection of trace concentration of $Pb^{2+}$ using poly(HPA) modified electrodes. For each concentration tested, a new polymer film was cast. The differential pulse stripping voltammograms (DPSV) for different concentrations of $Pb^{2+}$ in a 100 mM MES buffer (pH 6.5) are shown in FIG. 34, and a calibration curve is shown in FIG. 35. The poly(HPA) modified glassy carbon electrode is capable of detecting concentrations as low as 10 ppb of lead (lower than the maximum contamination limit) recommended by the US EPA.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for performing voltammetry to detect one or more metals in a sample, comprising the steps of:
   a) contacting the sample with an electrochemical tongue, the electrochemical tongue comprising:
      i) a reference electrode;
      ii) a counter electrode;
      iii) one or more working electrodes, wherein at least one of the one or more working electrodes is coated with a polymer or copolymer having the formula:

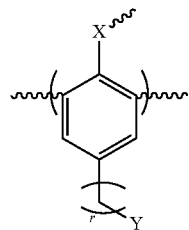

wherein X is O;
   r is an integer from 1 to 15; and
   Y is a carboxylic acid; and
   iv) a potentiostat in electrical communication with the reference electrode, the counter electrode, and the one or more working electrodes;
   b) applying a constant voltage across the one or more of the working electrodes to reduce the metal onto the surface of the one or more working electrodes; and
   c) increasing the voltage across the one or more working electrodes to oxidize and strip the metal from the surface of the one or more working electrodes; thereby detecting one or more metals in the sample.

2. The method of claim 1, wherein the electrochemical tongue has at least two working electrodes of distinct materials to which the sample is contacted.

3. The method of claim 2, wherein at least one of the one or more working electrodes are formed from gold, carbon fiber, silver, platinum, and transparent conductive oxides.

4. The method of claim 2, wherein at least one of the one or more working electrodes to which a sample is contacted includes at least one carbon-based material selected from the group consisting of glassy carbon; carbon paste; carbon fiber; carbon nanotubes; and graphene.

5. The method of claim 2, wherein at least one of the working electrodes to which a sample is contacted comprises conductive metal oxides coated on rigid or flexible substrates.

6. The method of claim 1, further comprising the steps of:
   d) applying a pulse voltage;
   e) measuring a first sampling current that flows through the one or more working electrodes during a predetermined interval in which the pulse voltage is not applied;
   f) measuring a second sampling current that flows through the one or more working electrodes while the pulse voltage is applied; and
   g) calculating the difference between the first and second sampling currents.

7. The method of claim 1, wherein r is 1.

8. The method of claim 1, wherein the electrochemical tongue has at least two working electrodes, and at least one of the one or more working electrodes is coated with poly(thiophene-co-n-Pyridin-4-yl-2-thiophen-3-yl-acetamide).

9. The method of claim 1, wherein the electrochemical tongue has at least two working electrodes, and at least one of the one or more working electrodes is coated with poly(thiophene acetic acid).

10. A method for performing voltammetry to detect one or more metals in a sample, comprising the steps of:
    a) contacting the sample with an electrochemical tongue, the electrochemical tongue comprising:
       i) a reference electrode;
       ii) a counter electrode;
       iii) one or more working electrodes, wherein at least one of the one or more working electrodes is coated with a polymer or copolymer having the formula:

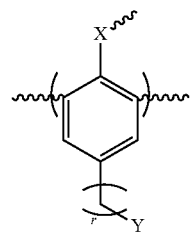

wherein X is O;
    r is an integer from 1 to 15; and
    Y is a carboxylic acid; and
    iv) a potentiostat in electrical communication with the reference electrode, the counter electrode, and the one or more working electrodes;

b) ramping the one or more working electrodes voltage linearly versus time to either positive or negative voltages, thereby detecting one or more metals in the sample.

11. The method of claim 10, wherein the electrochemical tongue has at least two working electrodes of distinct materials to which the sample is contacted.

12. The method of claim 11, wherein at least one of the one or more working electrodes are formed from gold, carbon fiber, silver, platinum, and transparent conductive oxides.

13. The method of claim 11, wherein at least one of the one or more working electrodes to which a sample is contacted includes at least one carbon-based material selected from the group consisting of glassy carbon; carbon paste; carbon fiber; carbon nanotubes; and graphene.

14. The method of claim 11, wherein at least one of the working electrodes to which a sample is contacted comprises conductive metal oxides coated on rigid or flexible substrates.

15. The method of claim 10, further comprising the steps of:

c) applying a pulse voltage;

d) measuring a first sampling current that flows through the one or more working electrodes during a predetermined interval in which the pulse voltage is not applied;

e) measuring a second sampling current that flows through the one or more working electrodes while the pulse voltage is applied; and f) calculating the difference between the first and second sampling currents.

16. The method of claim 10, wherein r is 1.

17. The method of claim 10, wherein the electrochemical tongue has at least two working electrodes, and at least one of the one or more working electrodes is coated with poly(thiophene-co-n-Pyridin-4-yl-2-thiophen-3-yl-acetamide).

18. The method of claim 10, wherein the electrochemical tongue has at least two working electrodes, and at least one of the one or more working electrodes is coated with poly(thiophene acetic acid).

* * * * *